(12) United States Patent
Schultz

(10) Patent No.: US 10,758,666 B1
(45) Date of Patent: Sep. 1, 2020

(54) OTORHINOLOGIC IRRIGATION SYSTEMS

(71) Applicant: Joseph P. Schultz, Atlanta, GA (US)

(72) Inventor: Joseph P. Schultz, Atlanta, GA (US)

( * ) Notice: Subject to any disclaimer, the term of this patent is extended or adjusted under 35 U.S.C. 154(b) by 203 days.

(21) Appl. No.: 14/169,012

(22) Filed: Jan. 30, 2014

Related U.S. Application Data

(60) Provisional application No. 61/911,921, filed on Dec. 4, 2013, provisional application No. 61/758,692, filed on Jan. 30, 2013.

(51) Int. Cl.
*A61M 3/02* (2006.01)

(52) U.S. Cl.
CPC ........ *A61M 3/0287* (2013.01); *A61M 3/0262* (2013.01)

(58) Field of Classification Search
CPC ...... A61M 16/0666; A61M 2039/0009; A61M 2039/0018
USPC .......................................... 604/187; 222/211
See application file for complete search history.

(56) References Cited

U.S. PATENT DOCUMENTS

| | | | | |
|---|---|---|---|---|
| 3,847,145 A | * | 11/1974 | Grossan | A61H 35/04 601/160 |
| 4,381,773 A | * | 5/1983 | Goodnow | A61D 7/00 128/200.14 |
| 4,878,903 A | * | 11/1989 | Mueller | A61M 3/0262 206/364 |
| 5,093,321 A | * | 3/1992 | Gottlieb | A61K 39/39 424/278.1 |
| 5,112,322 A | | 5/1992 | Hathaway | |
| 5,429,599 A | * | 7/1995 | Heinke | A61D 7/00 604/192 |
| 5,743,256 A | * | 4/1998 | Jalowayski | A61B 5/085 128/201.18 |
| 5,788,683 A | * | 8/1998 | Martin | A61M 1/0023 604/319 |
| 6,520,384 B2 | | 2/2003 | Mehta | |
| 7,288,083 B2 | | 10/2007 | Holman | |
| 8,652,117 B2 | * | 2/2014 | Ahnblad | A61M 3/0262 604/27 |
| 2002/0169422 A1 | * | 11/2002 | Ahnblad | A61H 35/04 604/217 |
| 2003/0145849 A1 | * | 8/2003 | Drinan | A61B 5/411 128/200.14 |
| 2005/0131357 A1 | * | 6/2005 | Denton | A61J 1/2096 604/275 |
| 2006/0253087 A1 | * | 11/2006 | Vlodaver | A61F 11/00 604/275 |
| 2007/0260189 A1 | * | 11/2007 | Shaw | A61M 5/347 604/187 |
| 2009/0297623 A1 | * | 12/2009 | O'Donnell, Jr. | A61K 9/0043 424/606 |

(Continued)

OTHER PUBLICATIONS

Sergio Ricardo Marques et al., "Morphometric Analysis of the Internal Auditory Canal by Computed Tomography Imaging", Iranian Journal of Radiology, Jun. 9, 2012(2): 71-78.

(Continued)

*Primary Examiner* — Imani N Hayman
(74) *Attorney, Agent, or Firm* — Merchant & Gould P.C.

(57) ABSTRACT

Systems, apparatus and methods related to improved otorhinologic irrigation and lavage comprising a drainage collector and one or more otorhinologic adapters, which are capable of coupling to an irrigation-liquid container.

34 Claims, 22 Drawing Sheets

(56) References Cited

U.S. PATENT DOCUMENTS

2012/0078166 A1    3/2012  Hoke et al.

OTHER PUBLICATIONS

"Small-bore Connectors—New Standards and Designs", May 31, 2014, AAMI2014 Conference & Expo May 31-Jun. 2, Philadelphia, pp. 1-44.

"Small-bore connectors for liquids and gases in healthcare applications—Part 7: Connectors for intravascular or hypodermic applications", International Standard ISO 80369-7, First Edition Oct. 15, 2016, Corrected version Dec. 1, 2016, Reference No. ISO 80369-7:2016(E), pp. 1-50.

Timothy R. Wolfe et al, "Intranasal Medication Delivery for Children: A Brief Review and Update", Pediatrics, Sep. 2010, vol. 126 / Issue 3, pp. 1-8.

\* cited by examiner

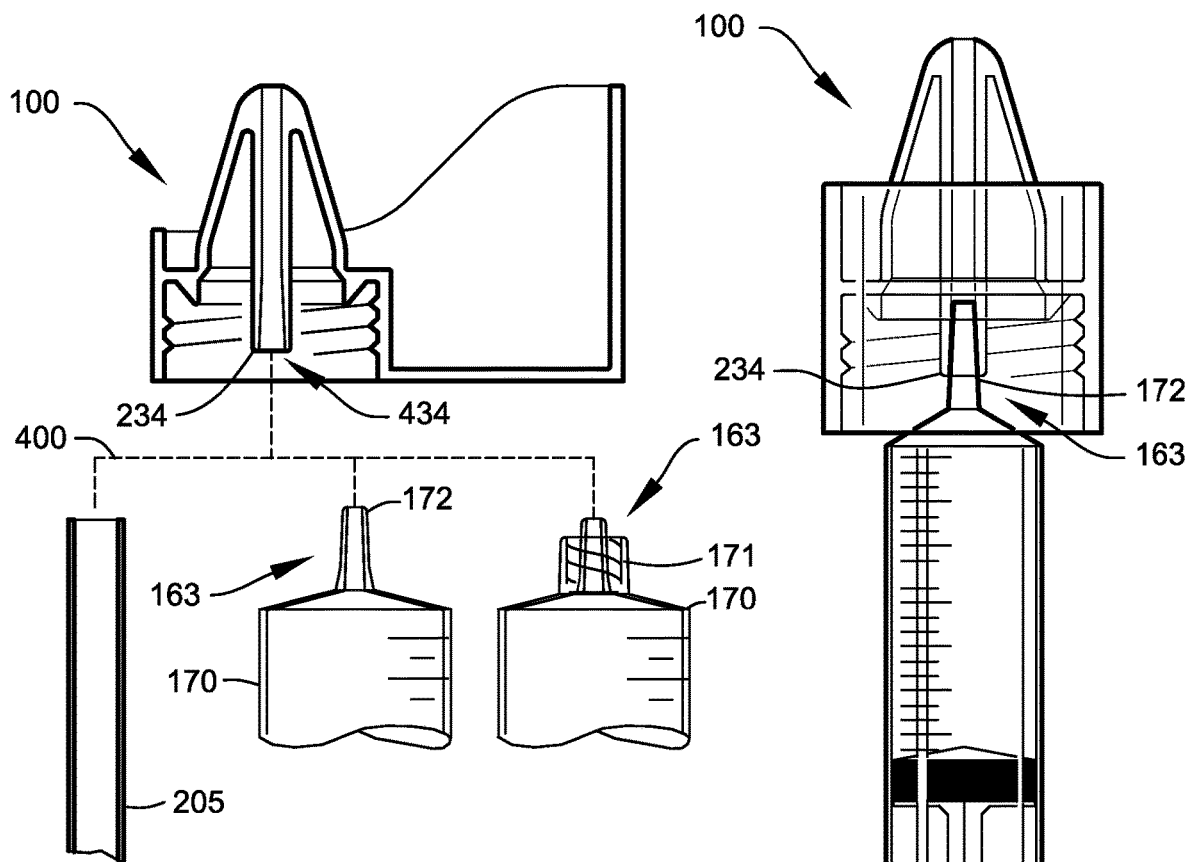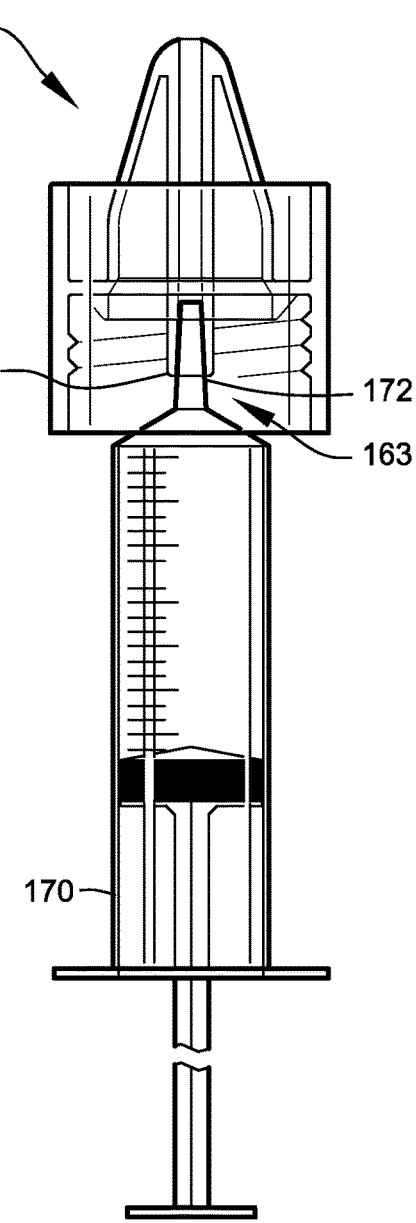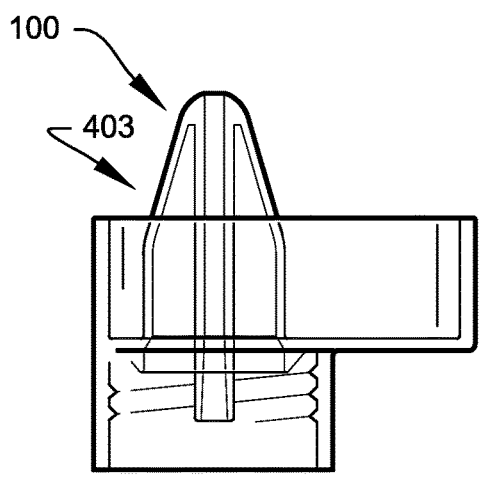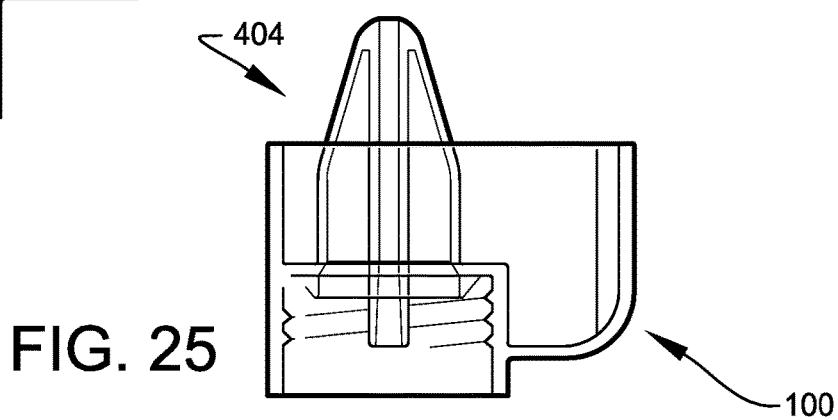
FIG. 22
FIG. 23
FIG. 24
FIG. 25

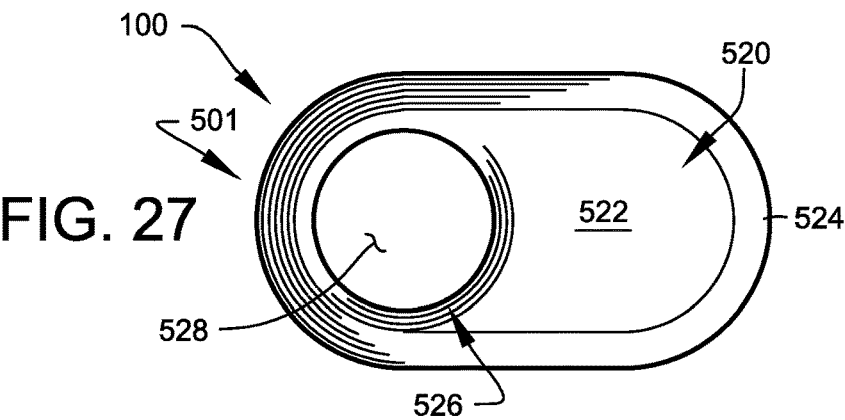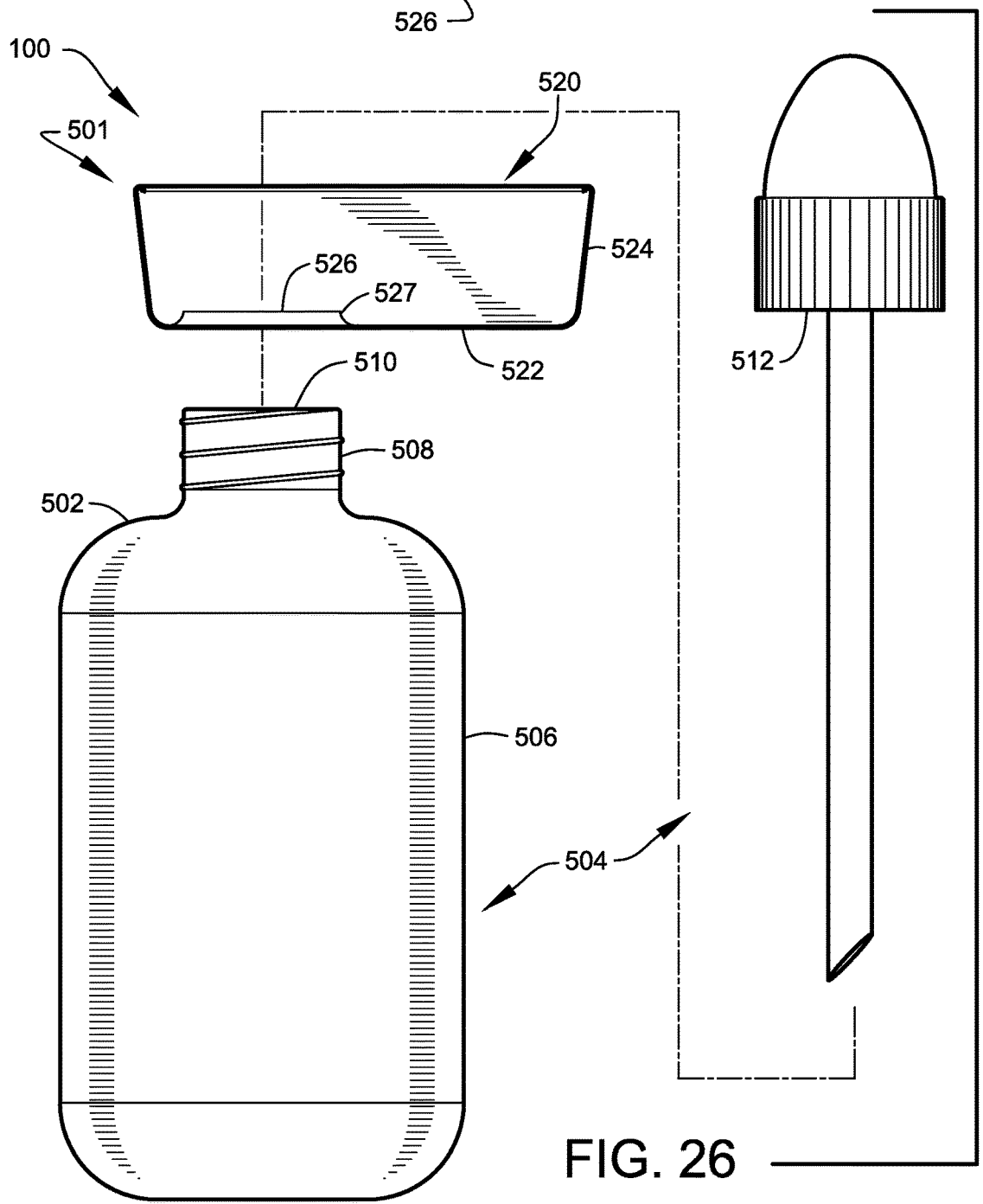

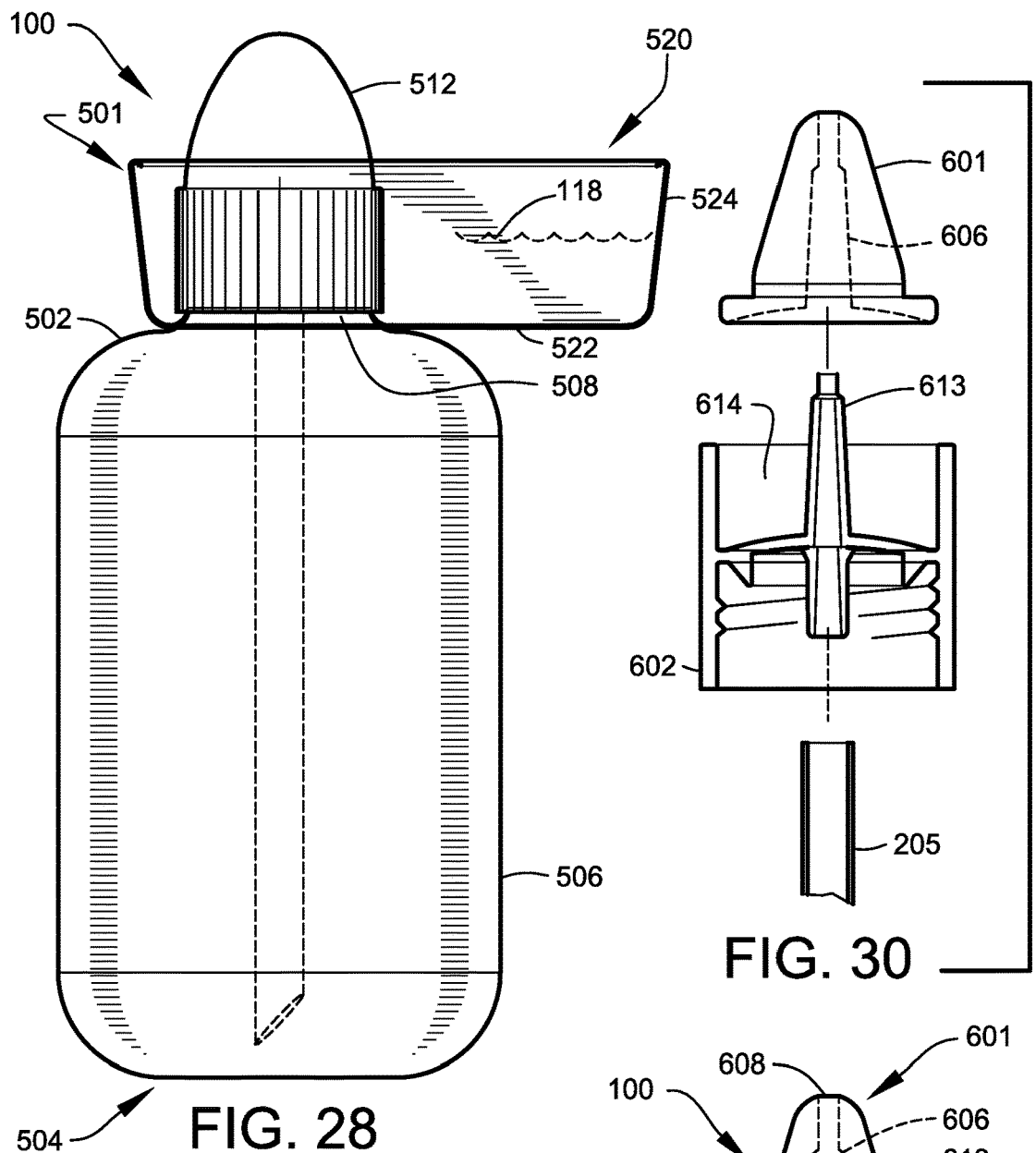
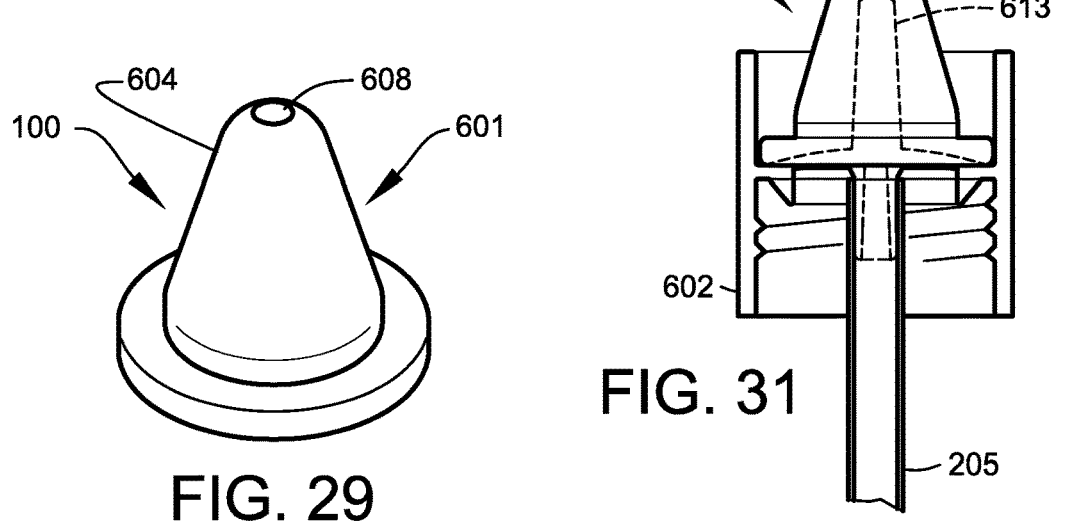
FIG. 28
FIG. 30
FIG. 29
FIG. 31

OTORHINOLOGIC IRRIGATION SYSTEMS

CROSS REFERENCE TO RELATED APPLICATION(S)

The present application is related to and claims priority form Provisional Application Ser. No. 61/911,921 filed Dec. 4, 2013, and from Provisional Application Ser. No. 61/758,692 filed Jan. 30, 2013, the contents of all of which are incorporated herein by this reference.

BACKGROUND

This invention relates to a medical system assisting more efficient and safer performance of otorhinologic medical procedures. More particularly, this invention concerns a medical system comprising apparatus and methods for improved ear-canal and nasal-passage irrigation.

With respect to ear canal irrigation problems, when a patient complains of a foreign body or cerumen impaction within the external ear canal, it is desirable to irrigate the external ear canal with a solution such as normal saline. Presumably the dilution effect of the irrigation will wash out cerumen and debris. A physician or user may wish to control the source and positioning of an irrigation stream. For example, improper positioning of an ear canal irrigation device may sometimes present the risk of trauma, e.g., to the external ear canal. A need exists for a device that will assist the physician or user with the proper positioning of an ear canal irrigation device.

With respect to nasal-passage irrigation problems, the procedure generally requires the patient's head to be located over a sink or similar catch basin. This is not always convenient for the patient or caregiver.

When using large volumes of liquid or high amounts of pressure, contaminated liquid may spread to unwanted surfaces, including splashing onto a health care provider or drenching the patient. This is undesirable as, e.g., the risk of spreading of disease is heightened and there may be undesirable effects of getting a patient wet. The excess liquid may also soil laundry and require increased housekeeping services, using existing methods of irrigation. The excess liquid may also be an inconvenience for otherwise healthy patients; they may have to remove their clothing to prevent them from getting soaked. The above situation may be uncomfortable for the patient in a busy emergency room; and, the time necessary for the patient to disrobe would delay a doctor's or nurse's ability to treat such patient or other waiting patients more expeditiously. These disadvantages may decrease the incentive for an operator, such as a physician, to appropriately use optimal large volumes of irrigation liquid, and therefore the difficulty of properly irrigating the ear canal increases.

A female threaded device does not exist that fit any of the commercially available standard wide-mouth irrigation pour bottles. There exists a need for a nasal irrigation device that fits these common sources of reliable sterile fluid to avoid having to stock additional nasal irrigation bottle fluid containers that can only be used for nasal irrigation. Furthermore, since at a single clinical location these standard wide mouth irrigation bottles may come from different suppliers at different times based on various market factors, there is a need for a device that is compatible with all three types of commercially-available standard wide-mouth irrigation pour bottles, so a nurse or physician does not lose valuable time, for example, in a busy emergency room, searching for a female threaded irrigation device compatible with each type of irrigation bottle, and so the supply chain purchasers do not have to order a different adapter for each commercial manufacturer of standard wide mouth irrigation bottles.

Furthermore, there exists a need for better irrigation devices using commonly available plunger syringes for flushing the nasal passages of children and adults using common sources of medical grade irrigation fluid such as standard wide mouth irrigation pour bottles and prefilled saline syringes.

OBJECTS AND FEATURES OF THE INVENTION

A primary object and feature of the present invention is to provide a system overcoming the above-mentioned problem(s).

It is a further object and feature of the present invention to provide an otorhinologic irrigation system for collecting liquid draining from an ear canal or nasal passage. It is another object and feature of the present invention to provide an otorhinologic irrigation system capable of assisting to prevent irrigation liquid from splashing onto a health care provider or drenching the patient.

It is a further object and feature of the present invention to provide an otorhinologic irrigation system capable of assisting with the proper positioning of an irrigation device within the ear canal. It is a further object and feature of the present invention to provide an otorhinologic irrigation system capable of easily accommodating connection with a variety of different sources of irrigation liquid. It is another object and feature of the present invention to provide a multi-purpose otorhinologic irrigation system comprising adapters capable adapting a multi-purpose otorhinologic irrigation device to a particular otorhinologic structure.

A further primary object and feature of the present invention is to provide such a system that is efficient, inexpensive, and useful. Other objects and features of this invention will become apparent with reference to the following descriptions.

SUMMARY OF THE INVENTION

In accordance with a preferred embodiment hereof, this invention provides a system, relating to procedures involving otorhinologic irrigation using a liquid, comprising: at least one liquid container comprising at least one manually-deformable internal reservoir structured and arranged to contain a volume of such liquid; in fluid communication with such at least one manually-deformable internal reservoir, at least one liquid injector structured and arranged to assist injection of the liquid into an otorhinologic structure of the head; at least one effluent collector structured and arranged to collect liquid-containing effluent draining from the otorhinologic structure; at least one coupler structured and arranged to removably couple such at least one liquid container with such at least one effluent collector; and at least one unifying connector structured and arranged to connect such at least one liquid injector, such at least one effluent collector, and such at least one coupler; wherein such at least one effluent collector comprises at least one cup-shaped member having at least one base wall and at least one surrounding wall projecting outwardly from such at least one base wall; wherein such at least one cup-shaped member comprises at least one splash shield structured and arranged to assist control of liquid splashing outside at least one effluent collector; wherein such at least one liquid injector comprises at least one anatomical adapter structured and arranged to adapt such at least one liquid injector to the anatomical geometry of at least one of at least one ear canal and at least one nasal passage; and wherein, when assembled, volumetric reductions of such at least manually-deformable internal reservoir by manual deformation assists such injection of such liquid from such at least one liquid injector.

Moreover, it provides such a system further comprising: such liquid; wherein such at least manually-deformable internal reservoir comprises a prefilled volume of such liquid. Additionally, it provides such a system wherein: the at least one liquid container comprises at least one threaded opening structured and arranged to permit discharge of such liquid from within such at least manually-deformable internal reservoir; and such at least one coupler comprises at least one threaded coupler structured and arranged to threadably engage such at least one threaded opening of such at least one liquid container. Also, it provides such a system wherein: such at least one liquid container comprises at least one standard wide-mouth irrigation pour bottle; such at least one threaded coupler and the at least one threaded opening, when tightly engaged, comprise at least one liquid seal structured and arranged to form at least one liquid-resistant seal between such at least manually-deformable internal reservoir of such at least one standard wide-mouth irrigation pour bottle and such at least one threaded coupler. In addition, it provides such a system wherein such at least one liquid injector comprises: at least one discharge port structured and arranged to discharge such liquid from such at least one liquid injector; and at least one liquid transport channel configured to assist the transport of such liquid between such at least manually-deformable internal reservoir and such at least one discharge port; wherein such at least one liquid injector is structured and arranged to project outwardly from such at least one base wall into such at least one effluent collector; and wherein such at least one discharge port is located distally of such at least one base wall.

And, it provides such a system further comprising: at least one liquid transport tube configured to assist transporting such liquid from at least one bottom interior portion of such at least one manually-deformable internal reservoir; wherein such at least one liquid transport tube is in fluid communication with such at least one liquid transport channel. Further, it provides such a system further comprising at least one transport-tube coupler configured to removably couple such at least one liquid transport tube to such at least one liquid transport channel. Even further, it provides such a system wherein such at least one transport-tube coupler comprises at least one syringe coupler configured to removably couple such at least one liquid transport channel to at least one liquid-delivery syringe. Moreover, it provides such a system wherein such at least one syringe coupler is configured to removably couple such at least one liquid transport channel to at least one liquid-delivery syringe having at least one Luer-type coupler.

Additionally, it provides such a system wherein such at least one surrounding wall comprises at least one distal opening comprising at least one wall-terminating periphery structured and arranged to encompass and fully surround at least one outer-ear structure. Also, it provides such a system wherein such at least one anatomical adapter comprises at least one liquid injector-port positional adjuster structured and arranged to assist user adjustments to the position of such at least one discharge port relative to such at least one base wall.

In addition, it provides such a system wherein such at least one anatomical adapter comprises: at least one extendable tube configured to extend into at least one ear canal of the head; wherein such at least one extendable tube comprise such at least one discharge port; wherein such at least one extendable tube is in fluid communication with such at least one liquid transport tube; wherein such at least one extendable tube is movably engaged within such at least one liquid transport channel; and wherein such at least one discharge port is adjustably positionable within the at least one ear canal of the head. And, it provides such a system wherein such at least one extendable tube comprises such at least one liquid transport tube. Further, it provides such a system wherein such at least one extendable tube comprises axial flexibility sufficient to generate shape conformance of such at least one extendable tube with the at least one ear canal. Even further, it provides such a system wherein such at least one surrounding wall comprises at least one pressure-relieving aperture structured and arranged to assist preventing harmful pressure differentials when irrigating the otorhinologic structure. Moreover, it provides such a system wherein such at least one liquid transport channel is symmetrically positioned relative to such at least one surrounding wall. Additionally, it provides such a system wherein: such at least one liquid transport channel is asymmetrically located relative to such at least one surrounding wall; and such non-central placement assists in directing such at least one discharge port into the at least one ear canal of the head when such at least one surrounding wall of such at least one effluent collector is in the position encompassing the at least one outer-ear structure.

Also, it provides such a system wherein: such at least one anatomical adapter comprises at least one nasal bulb configured to sealingly engage a nostril of the at least one nasal passage; and such at least one nasal bulb comprises such at least one discharge port. In addition, it provides such a system wherein such at least one nasal bulb is configured to be removable from such at least one liquid injector. And, it provides such a systems wherein such at least one liquid injector, such at least one effluent collector, and such at least one coupler comprise a single monolithically-formed material.

In accordance with another preferred embodiment hereof, this invention provides a system, relating to procedures involving otorhinologic irrigation using a liquid supplied from at least one liquid container comprising at least one manually-deformable internal reservoir, such system comprising: at least one liquid injector structured and arranged to assist injection of the liquid into an otorhinologic structure of the head; at least one effluent collector structured and arranged to collect liquid-containing effluent draining from the otorhinologic structure; at least one coupler structured and arranged to removably couple the at least one liquid container with such at least one effluent collector; and at least one unifying connector structured and arranged to connect such at least one liquid injector, such at least one effluent collector, and such at least one coupler; wherein such at least one effluent collector comprises at least one cup-shaped member having at least one base wall and at least one surrounding wall projecting outwardly from such at least one base wall; wherein such at least one cup-shaped member comprises at least one splash shield structured and arranged to assist control of liquid splashing outside at least one effluent collector; wherein such at least one liquid injector comprises at least one anatomical adapter structured and arranged to adapt such at least one liquid injector to the physical geometry of at least one of at least one ear canal and at least one nasal passage; and wherein, when, volumetric reductions of such at least manually-deformable internal reservoir by manual deformation assists such injection of such liquid from such at least one liquid injector.

Further, it provides such a system wherein: the at least one liquid container comprises a prefilled standard wide-mouth irrigation pour bottle having at least one threaded opening structured and arranged to permit discharge of the liquid from within the at least manually-deformable internal reservoir; and such at least one coupler comprises at least one threaded coupler structured and arranged to threadably engage such at least one threaded opening of such at least one liquid container; wherein such at least one threaded coupler and the at least one threaded opening, when tightly engaged, comprise at least one liquid seal structured and arranged to form at least one liquid-resistant seal between the at least manually-deformable internal reservoir of the at least one standard wide-mouth irrigation pour bottle and such at least one threaded coupler. Even further, it provides such a system wherein such at least one liquid injector comprises: at least one discharge port structured and arranged to discharge the liquid from such at least one liquid injector; and at least one liquid transport channel configured to assist the transport of the liquid between such at least manually-deformable internal reservoir and such at least one discharge port; wherein such at least one liquid injector is structured and arranged to project outwardly from such at least one base wall into such at least one effluent collector; and wherein such at least one discharge port is located distally of such at least one base wall.

Moreover, it provides such a system further comprising: at least one liquid transport tube configured to assist transporting the liquid from at least one bottom interior portion of the at least one manually-deformable internal reservoir; wherein such at least one liquid transport tube is in fluid communication with the at least one liquid transport channel. Additionally, it provides such a system further comprising at least one transport-tube coupler configured to removably couple such at least one liquid transport tube to such at least one liquid transport channel. Also, it provides such a system wherein: such at least one transport-tube coupler comprises at least one syringe coupler configured to removably couple such at least one liquid transport channel to at least one liquid-delivery syringe. In addition, it provides such a system wherein such at least one syringe coupler is configured to removably couple such at least one liquid transport channel to at least one liquid-delivery syringe having at least one Luer-type coupler. And, it provides such a system wherein such at least one surrounding wall comprises at least one distal opening having at least one wall-terminating periphery structured and arranged to encompass and fully surround at least one outer-ear structure. Further, it provides such a system wherein such at least one anatomical adapter comprises at least one liquid injector-port positional adjuster structured and arranged to assist user adjustments to the position of such at least one discharge port relative to such at least one base wall.

Even further, it provides such a system wherein such at least one anatomical adapter comprises: at least one extendable tube configured to extend into at least one ear canal of the head; wherein such at least one extendable tube comprise such at least one discharge port; wherein such at least one extendable tube is in fluid communication with such at least one liquid transport tube; wherein such at least one extendable tube is movably engaged within such at least one liquid transport channel; and wherein such at least one discharge port is adjustably positionable within the at least one ear canal of the head. Moreover, it provides such a system wherein such at least one extendable tube comprises such at least one liquid transport tube. Additionally, it provides such a system wherein such at least one extendable tube comprises axial flexibility sufficient to generate shape conformance of such at least one extendable tube with the at least one ear canal. Also, it provides such a system wherein such at least one surrounding wall comprises at least one pressure-relieving aperture structured and arranged to assist preventing harmful pressure differentials when irrigating the otorhinologic structure. In addition, it provides such a system wherein such at least one liquid transport channel is symmetrically positioned relative to such at least one surrounding wall. And, it provides such a system wherein: such at least one liquid transport channel is asymmetrically located relative to such at least one surrounding wall; and such non-central placement assists in directing such at least one discharge port into the at least one ear canal of the head when such at least one surrounding wall of such at least one effluent collector is in the position encompassing the at least one outer-ear structure.

Further, it provides such a system wherein: such at least one anatomical adapter comprises at least one nasal bulb configured to sealingly engage a nostril of the at least one nasal passage; and such at least one nasal bulb comprises such at least one discharge port. Even further, it provides such a system wherein such at least one nasal bulb is configured to be removable from such at least one liquid injector. Even further, it provides such a systems wherein such at least one liquid injector, such at least one effluent collector, and such at least one coupler comprise a single monolithically-formed material.

In accordance with another preferred embodiment hereof, this invention provides a system, relating to improved irrigation of a nasal passage using a bottle having flexible sidewalls and a bottle-neck opening for a removable cap wherein the cap comprises a nasal-engaging opening at the cap's uppermost surface, the nasal-engaging opening being in fluid communication with an interior portion of the container, such system comprising the improvement of: at least one effluent collector structured and arranged to collect effluent draining from the nasal passage during such irrigation; wherein such at least one effluent collector comprises at least one coupler structured and arranged to couple such to at least one effluent collector. Even further, it provides such a systems wherein such at least one effluent collector further comprises: at least one cup-shaped member having at least one base wall and at least one surrounding wall projecting outwardly from such at least one base wall; wherein such at least one coupler comprises at least one aperture opening located within such base wall, such at least one aperture opening structured and arranged to pass the bottle-neck opening therethough. Even further, it provides such a systems wherein such at least one effluent collector, when coupled with the bottle, is retained to the bottle-neck opening by the removable cap.

In accordance with other preferred embodiments hereof, this invention provides each and every novel feature, element, combination, step and/or method disclosed or suggested by this patent application.

BRIEF DESCRIPTION OF THE DRAWINGS

FIG. 22 shows an exploded view, in partial section, illustrating diagrammatically, the coupling of a preferred embodiment of the present invention to one of multiple liquid supply sources.

FIG. 23 shows a side view illustrating the coupling of a preferred embodiment of the present invention to a medical syringe, according to the preferred embodiments of the present invention.

FIG. 24 shows a side view of an alternate embodiment of the present invention.

FIG. 25 shows a side view of an alternate embodiment of the present invention.

FIG. 26 shows an exploded view, illustrating a nasal effluent collector attachable to an existing nasal irrigation bottle, according to another preferred embodiment of the present invention.

FIG. 27 shows a top view, illustrating the nasal effluent collector of FIG. 26.

FIG. 28 shows a side view, illustrating the nasal effluent collector attached in an operable position to the existing nasal irrigation bottle of FIG. 26.

FIG. 29 shows a perspective view, illustrating a nasal irrigation adapter attachable to an existing medical irrigation device, according to another preferred embodiment of the present invention.

FIG. 30 shows an exploded side view, in partial section, illustrating the nasal irrigation adapter of FIG. 29 and associated components.

FIG. 31 shows a side view, in partial section, illustrating the nasal irrigation adapter of FIG. 29 and associated components in an assembled configuration.

FIG. 39 B shows the adapter of FIG. 39A connected to a squeeze bottle having a dip tube.

DETAILED DESCRIPTION OF THE BEST MODES AND PREFERRED EMBODIMENTS OF THE INVENTION

Figure 1A:
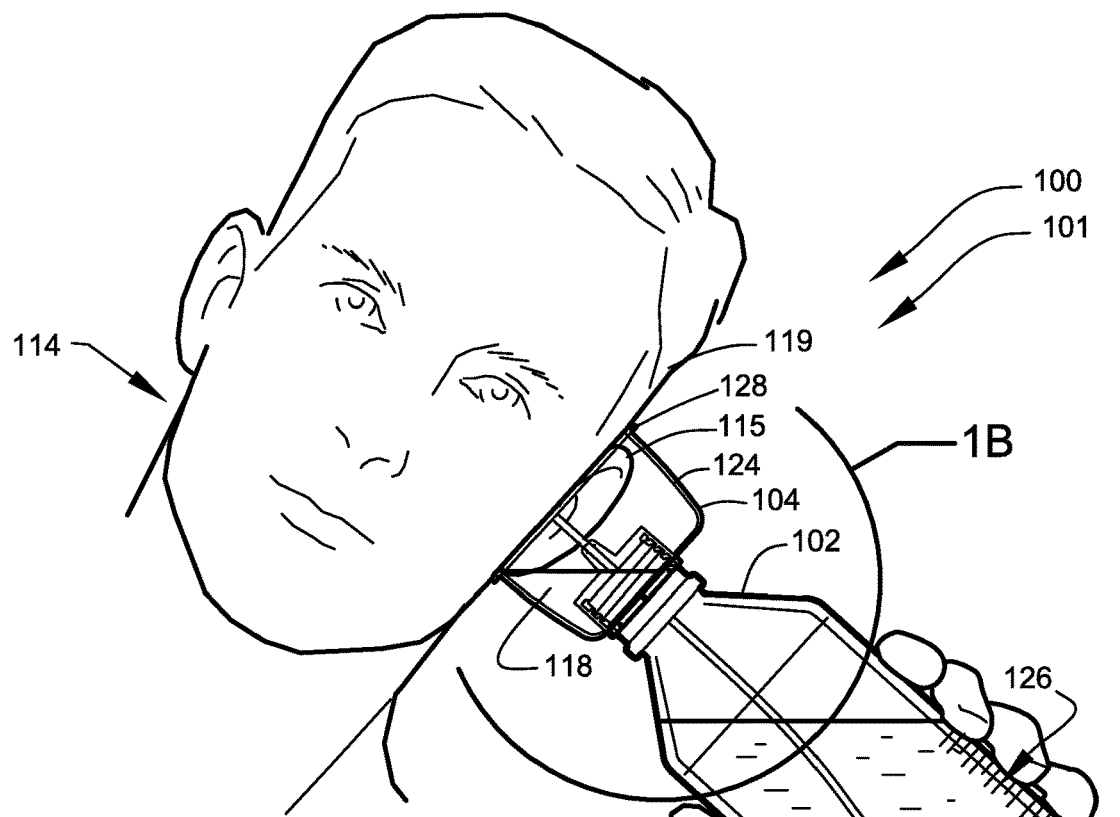
FIG. 1A shows a front-facing view, illustrating the use of an assembled ear irrigator of the otorhinologic irrigation system, according to a preferred embodiment of the present invention.
Figure 1B:
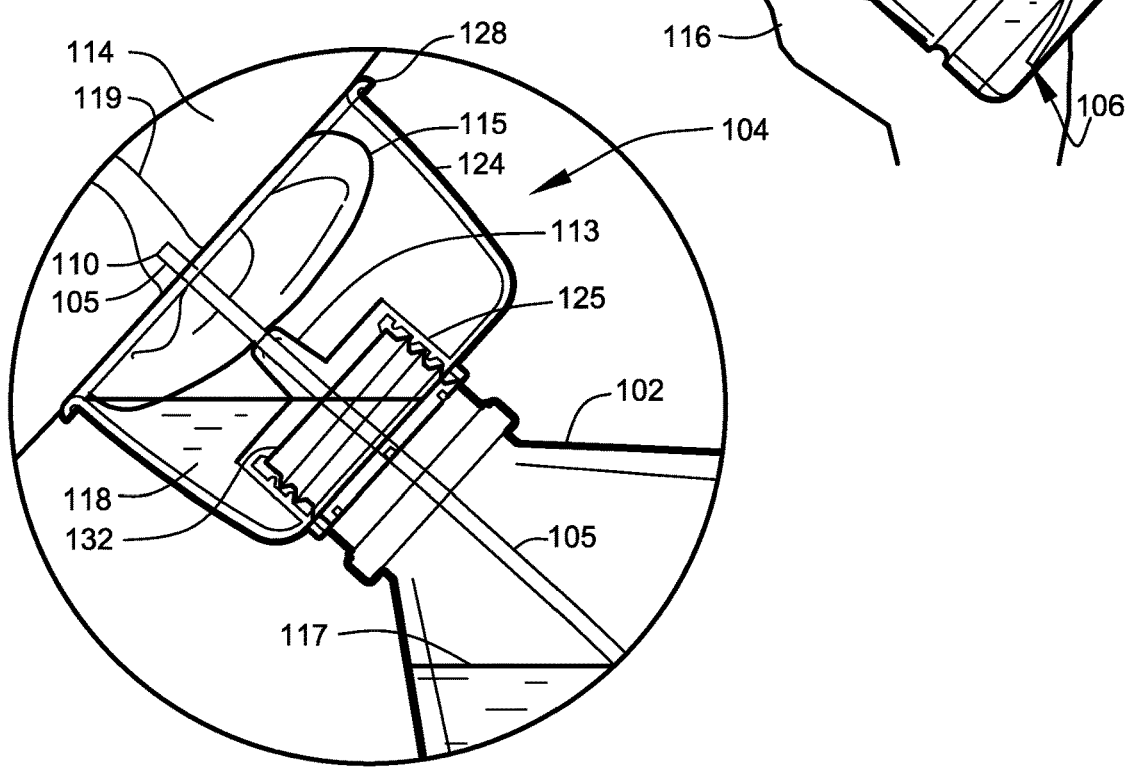
FIG. 1B shows a detail view illustrating the assembled ear irrigator of FIG. 1A.

The present-disclosed system pertains to medical systems assisting more efficient and safer performance of otorhinologic medical procedures. More particularly, the present system comprises apparatus and methods for improved ear-canal and nasal-passage irrigation. FIG. 1A shows the use of an assembled ear irrigator 101 of the otorhinologic irrigation system 100 according to a preferred embodiment of the present invention. FIG. 1B shows a detail view of the assembled ear irrigator 101 of FIG. 1A.

Assembled ear irrigator 101 preferably comprises an injector tube 105, and an effluent collector 104 that has been removably attached to irrigation squeeze bottle 102. Injector tube 105 preferably comprises a tube inlet 106 that preferably is located inside of irrigation squeeze bottle 102, and a tube outlet 110 that preferably is located outside of effluent collector 104, as shown. Tube outlet 110 preferably extends past mouth 128 of cup 124 a preferred distance of about one-quarter inch to about three inches. Cup 124 preferably comprises a base wall 141 and surrounding wall 142. In one preferred embodiment, tube outlet 110 preferably extends past mouth 128 of cup 124 a preferred distance of about one inch. Upon reading the teachings of this specification, those of ordinary skill in the art will now understand that, under appropriate circumstances, considering issues such as ear size, ear depth, etc., other distance in which tube outlet extends beyond mouth, such as four inches, one-eighth inch, five inches, etc., may suffice.

Effluent collector 104 preferably comprises at least one cup 124 preferably having a generally frustoconical shape, preferably at least one cylindrical member 125 and preferably at least one nozzle portion 113. Nozzle portion 113 preferably is concentrically located within cylindrical member 125, as shown. Cup 124, cylindrical member 125 and nozzle portion 113 preferably are rigidly connected to each other, as shown, and are formed as a single monolithic piece. Injector tube 105 preferably extends from the interior bottom of irrigation squeeze bottle 102, passes through nozzle portion 113 (at least herein embodying at least one injector structured and arranged to be projected outwardly from said at least one base wall into said at least one collector), and extends outward from effluent collector 104, as shown.

Upon reading the teachings of this specification, those of ordinary skill in the art will understand that, under appropriate circumstances, considering such issues as design preference, user preferences, marketing preferences, cost, structural requirements, available materials, technological advances, etc., other designs, such as e.g. an apertured cylindrical member without a nozzle, or a nozzle having e.g. a straight cylinder, stepped, inverted, etc. configuration, or other injector tube guiding structure may suffice.

In ordinary use, a user 114 preferably gently inserts tube outlet 110 of injector tube 105 within their (or the ear canal of another) ear canal 119 while simultaneously placing the open end of cup 124 around the ear 115. With tube outlet 110 located slightly within ear canal 119, user 114 preferably gently presses the assembled ear irrigator 101 against the head, as shown. Upon reading this specification, those with ordinary skill in the art will now appreciate that, under appropriate circumstances, considering such issues as design preference, user preferences, marketing preferences, cost, structural requirements, available materials, technological advances, etc., other useful arrangements such as, e.g., near the head, partially against the side of the head, etc., may suffice.

Next, preferably, assembled ear irrigator 101 is kept pressed against the head, preferably user 114 tilts his or her head by about 45-degrees from vertical towards ear 115 and then squeezes irrigation squeeze bottle 102 (preferably with at least one hand 116). It is noted that assembled ear irrigator 101 may preferably also be used in an "upright" vertical orientation or in a horizontal orientation. Irrigation squeeze bottle 102 preferably is hand-held and hand squeezable. Squeezing irrigation squeeze bottle 102 preferably deforms the outer wall 126 (at least herein embodying at least one liquid container comprising at least one hand-deformable region structured and arranged to assist liquid injection) of irrigation squeeze bottle 102 so as to reduce the internal volume of the manually-deformable internal reservoir 107 of irrigation squeeze bottle 102. Deforming outer wall 126 increases the pressure on irrigation liquid 117 contained within the manually-deformable internal reservoir 107, preferably forcing that irrigation liquid 117 into tube inlet 106, through injector tube 105, and out tube outlet 110 (at least herein embodying at least one discharge port structured and arranged to discharge the liquid from said at least one injector) preferably into the ear canal 119. When user 114 applies pressure to irrigation squeeze bottle 102, a stream of irrigation liquid 117 emits from tube outlet 110 (at least herein embodying at least one injector structured and arranged to inject the liquid into an ear canal) and irrigates ear canal 119. Upon reading the teachings of this specification, those skilled in the art will now appreciate that, under appropriate circumstances, considering such issues as design preference, user preferences, medical needs, marketing preferences, cost, structural requirements, available materials, technological advances, etc., other discharge methods e.g. manual or electrical pumping, etc. may suffice.

Liquid-containing effluent 118 draining from the irrigation of ear canal 119 preferably flows into cup 124 (at least herein embodying at least one collector structured and arranged to collect liquid draining from an ear canal) which acts as a splash shield to assist preventing the liquid from splashing outside the cup of effluent collector 104 (at least herein embodying at least one collector comprising at least one splash shield structured and arranged to assist control of liquid splashing outside at least one collector), as shown. Cup 124 is preferably transparent so as to provide a view of the liquid-containing effluent 118 while it is collected within cup 124 (at least herein embodying at least one splash shield comprising at least one transparent portion configured to provide a view of the liquid, discharged into said at least one collector from the ear canal), where it may be examined by a Physician (or a user) and discarded. This arrangement at least embodies herein wherein such at least one cup-shaped member comprises at least one splash shield structured and arranged to assist control of liquid splashing outside at least one effluent collector. Cup 124 preferably holds a volume between about 50 cubic centimeters and 300 cubic centimeters. In one preferred embodiment, cup 124 holds a volume of about 150 cubic centimeters (cc). Upon reading the teachings of this specification, those of ordinary skill in the art will now understand that, under appropriate circumstances, considering issues such as ear size, amount of liquid to be collected, etc., other volumes of cup, such as 200 cubic centimeters, 25 cubic centimeters, etc., may suffice. Cup 124 preferably has an inner diameter between about two inches and five inches. In one preferred embodiment, cup 124 has an inner diameter of about two and three-quarters inches. Upon reading the teachings of this specification, those of ordinary skill in the art will now understand that, under appropriate circumstances, considering issues such as ear size, subject type (animal vs. human), other inner diameter dimensions may suffice.

Figure 2A:
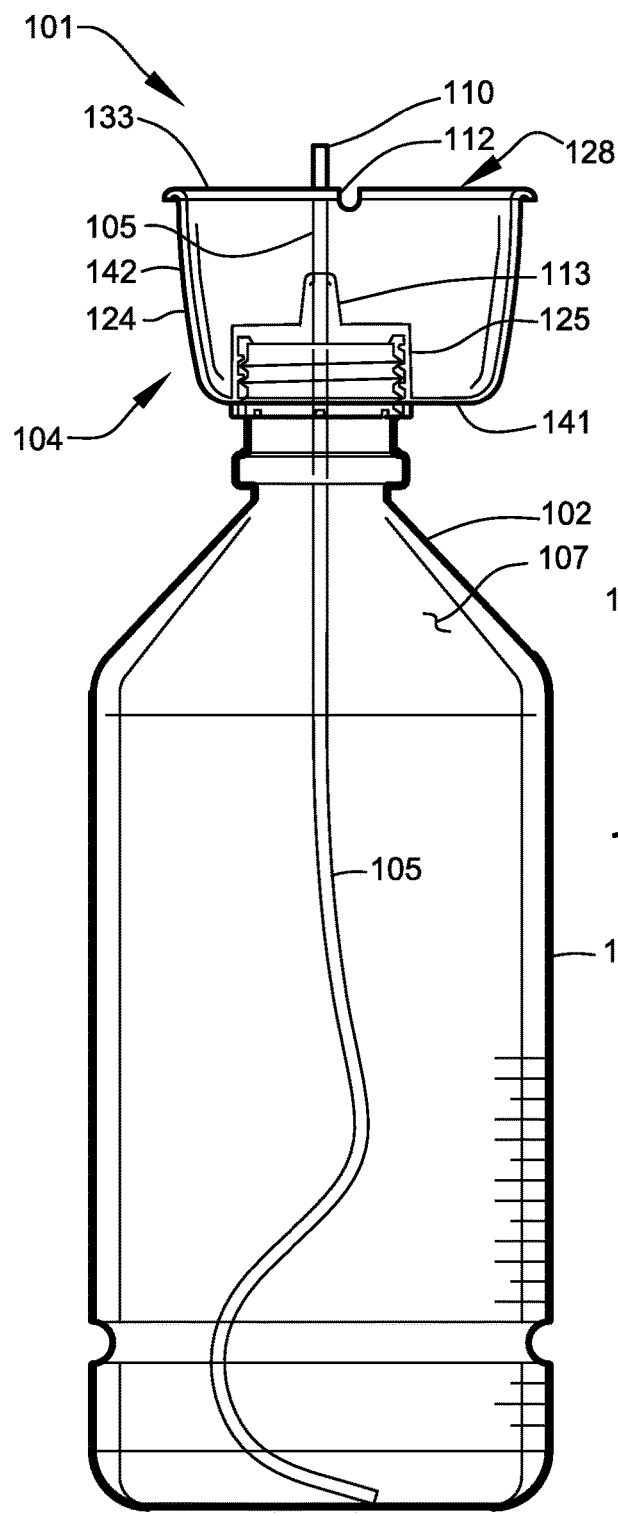
FIG. 2A shows a front view illustrating the assembled ear irrigator, according to the preferred embodiment of FIG. 1.
Figure 2B:
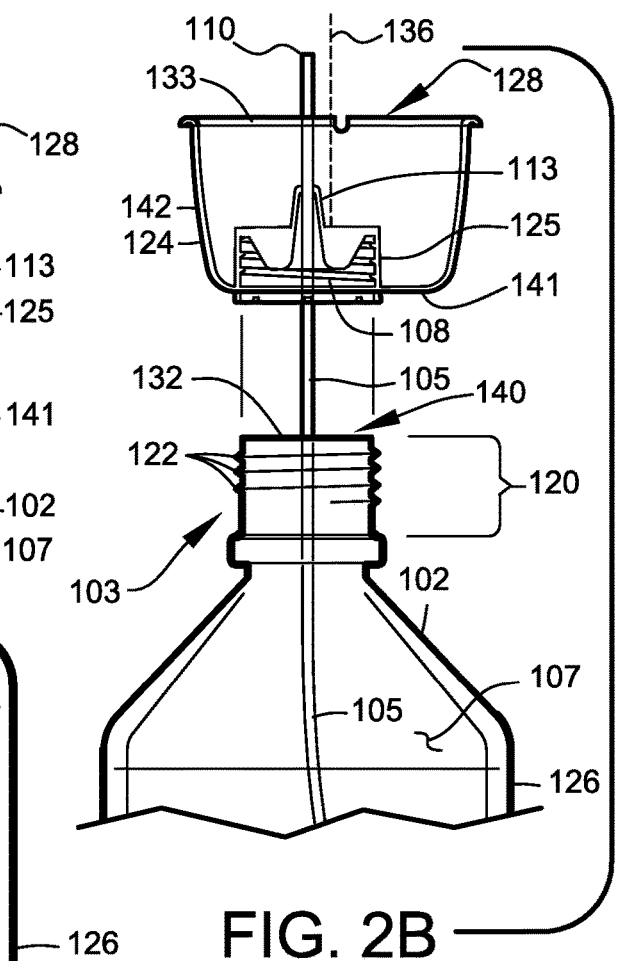
FIG. 2B shows a front view, partially in section, illustrating the assembled ear irrigator of FIG. 2A.

FIG. 2A is a front view of the assembled ear irrigator 101 according to the preferred embodiment of FIG. 1. FIG. 2B is a front view, partially in section, of the assembled ear irrigator 101 of FIG. 2A.

Assembled ear irrigator 101 preferably comprises at least one effluent collector 104, preferably one effluent collector 104, at least one irrigation squeeze bottle 102 (more than one may need to be used to irrigate the ear), and injector tube 105, as shown. Effluent collector 104 preferably comprises cup 124, cylindrical member 125, and nozzle portion 113, as shown. Cup 124 preferably is open at one end comprising mouth 128, as shown. Mouth 128 preferably is circular in shape and comprises a perimeter 133. Perimeter 133 preferably has a geometric center 136. Preferred irrigation squeeze bottles 102 comprise standard wide-mouth standard irrigation pour bottles. Preferred irrigation squeeze bottle 102 include bottles of polymer construction, formed from a manually deformable (squeezable) plastic. Irrigation squeeze bottle 102 preferably contains a bulk volume of irrigation liquid 117. One preferred irrigation liquid suitable for use as irrigation liquid 117 comprises a normal saline solution of sodium chloride (NaCl) dissolved in water. Other preferred irrigation liquids include both sterile and non-sterile lactated ringers, balanced salt solutions, tap water, and the like. The bulk volume of irrigation liquid 117 contained in irrigation squeeze bottle 102 is preferably supplied in volumes ranging between about 250 cc (cubic centimeters) and about 2000 cc. Irrigation squeeze bottle 102 preferably comprises a semi-rigid (but manually deformable) outer wall 126 enclosing a manually-deformable internal reservoir 107. The outer wall 126 preferably comprises a narrowed cylindrical neck 103 terminating at a mouth-opening 140 (at least herein embodying at least one liquid container comprising at least one threaded opening structured and arranged to permit discharge of the liquid from within said at least one liquid container) for discharging the liquid contents of the irrigation squeeze bottle 102. The top edge of cylindrical neck 103, which surrounds mouth-opening 140, comprises bottle lip 132. Bottle lip 132 preferably is smoothly finished. Cylindrical neck 103 has external helical threads 122 and comprises a male coupling 120.

As described and illustrated herein, effluent collector 104 in combination with injector tube 105 preferably form an assembly 150 that may be coupled to at least one, and preferably a plurality of, irrigation squeeze bottles 102, as shown. Upon reading this specification, those skilled in the art will now appreciate that, under appropriate circumstances, considering such issues as design preference, user preferences, marketing preferences, cost, structural requirements, available materials, technological advances, etc., other coupling arrangements, such as, for example, coupling to a syringe, coupling to a larger reservoir of liquid, etc., may suffice.

Figure 3:
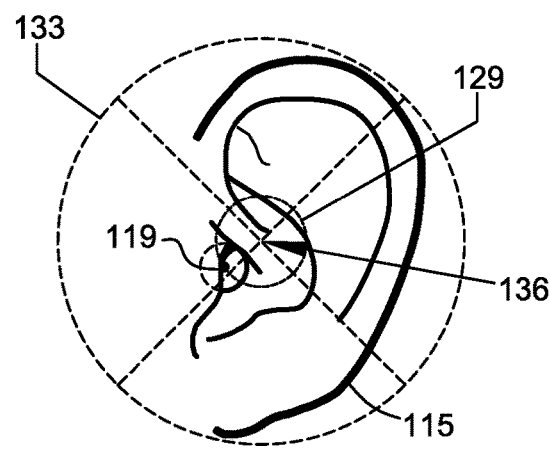
FIG. 3 shows a perspective view, illustrating a typical human ear relative to the perimeter of the mouth of a drainage collector cup of an ear irrigator, according to a preferred embodiment of the present invention.

FIG. 3 is a perspective view illustrating a typical human ear 115 relative to the perimeter 133 of the mouth 128 of cup 124. When an ear 115 is located within the mouth 128 of cup 124, the ear canal 119 preferably and generally is not anatomically located at the center 136 of the perimeter 133 of the mouth 128. Preferably, effluent collector 104 is manufactured so that ear canal 119 is offset from the center 136 of mouth 128 by at least one offset radius 129, as shown and further described below.

Figure 4:
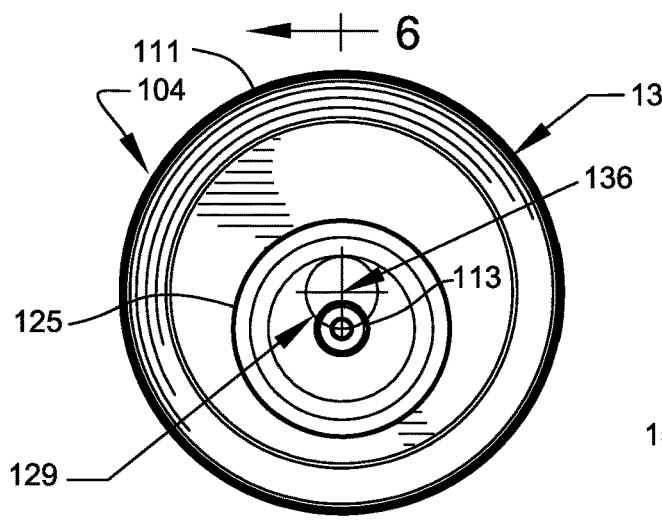
FIG. 4 shows a top view illustrating a drainage collector, according to the preferred embodiment of FIG. 2A.
Figure 5:
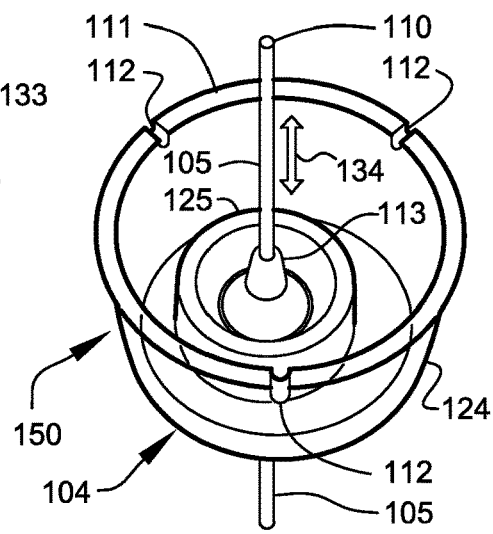
FIG. 5 shows a perspective top view of the drainage collector, according to the preferred embodiment of FIG. 2A.
Figure 6:
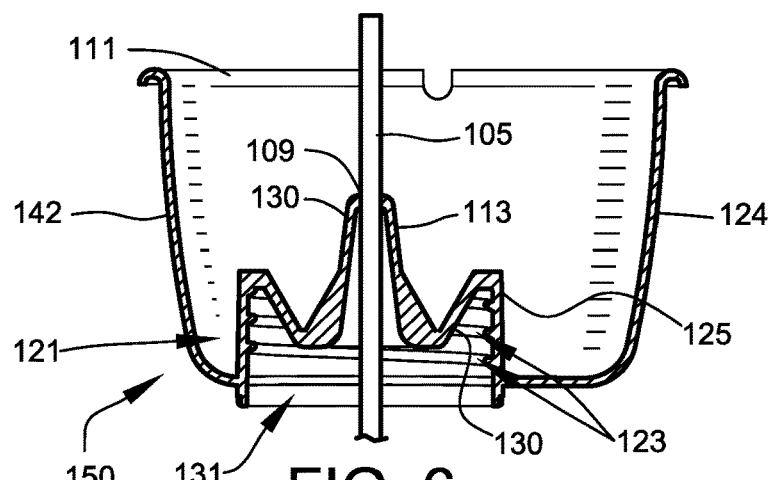
FIG. 6 shows a sectional view through section 6-6 of FIG. 4.

FIG. 4 is a top view of an effluent collector 104 according to the preferred embodiment of FIG. 2A. FIG. 5 is a perspective top view of the effluent collector 104 according to the preferred embodiment of FIG. 2A. FIG. 6 is a sectional view through section 6-6 of FIG. 4.

Nozzle portion 113 preferably is located centrally within cylindrical member 125, as shown. Nozzle portion 113 preferably is located in a position offset from the center 136 of cup 124 and preferably is located along an offset radius 129 (at least herein embodying at least one internal bore is not centrally placed relative to said base wall) extending from center 136. Offset radius 129 comprises an imaginary circle of all points preferably located about six millimeters, more preferably about 6.35 millimeters, from the center 136 of cup 124. Thus, when cup 124 encloses an average ear 115, the offset center of nozzle portion 113 preferably will substantially align with the center of ear canal 119, as shown. Upon reading this specification, those with ordinary skill in the art will now appreciate that, under appropriate circumstances, considering such issues as design preference, user preferences, marketing preferences, cost, structural requirements, available materials, technological advances, ear size, human or animal ear, etc., other drainage collector ear canal alignment arrangements such as, e.g., offset, skewed, centered, etc., may suffice.

Effluent collector 104 preferably comprises cup 124, cylindrical member 125, and nozzle portion 113 and injector tube 105 (assembly 150). Preferably, effluent collector 104, cup 124, cylindrical member 125 and nozzle portion 113 (including threaded elements described below) comprise a single monolithically-molded polymer, alternately preferably a medical-grade plastic (at least herein embodying a system wherein at least one injector, at least one collector, and at least one coupler comprise a single monolithically-molded polymer).

Nozzle portion 113 preferably is substantially hollow and preferably comprises a smoothbore aperture 109 at its tip. Smoothbore aperture 109 (at least herein embodying at least one positional support comprising friction between said at least one internal bore and external surfaces of said at least one flexible tube) preferably is sized to provide a friction fit to injector tube 105. Injector tube 105 preferably is about a 30 centimeter long, size 10-French catheter. Upon reading this specification, those with ordinary skill in the art will now appreciate that, under appropriate circumstances, considering such issues as design preference, user preferences, marketing preferences, cost, structural requirements, available materials, technological advances, etc., other catheter arrangements such as, e.g., larger or smaller, one or more micro-catheters, etc., may suffice.

Injector tube 105 preferably is inserted through the smoothbore aperture 109 of nozzle portion 113 and extends outward from effluent collector 104, as shown. Injector tube 105 preferably is movably secured against sliding by a friction fit with smoothbore aperture 109. The friction fit provided by smoothbore aperture 109 preferably constrains injector tube 105 from substantially all motion except for a length adjustment 134 (at least herein embodying at least one positional support structured and arranged to positionally support said at least one flexible tube), as shown. User 114 preferably may adjust the length of injector tube 105 by applying force sufficient to overcome the friction fit. Upon reading this specification, those skilled in the art will now appreciate that, under appropriate circumstances, considering such issues as design preference, user preferences, marketing preferences, cost, structural requirements, available materials, technological advances, etc., other injector tube constraint arrangements within smoothbore aperture such as, for example, mechanical constraints, adhesive constraints, flexible rubber sealant, etc., may suffice.

The mouth opening of cup 124 preferably comprises at least one lip 111 preferably comprising at least one perimeter 133. Perimeter 133 is preferably circular in shape and preferably comprises a diameter of about three inches, more preferably about three and one-quarter inches. Lip 111 preferably terminates the sidewall of cup 124 preferably about two inches distally from the bottom of cup 124 (at least herein embodying at least one cup-shaped member having at least one base wall and at least one surrounding wall projecting outwardly from said at least one base wall) thereby providing cup 124 with, preferably, about two inches of depth. The above-described arrangement at least herein embodies wherein said at least one surrounding wall comprises at least one distal opening comprising at least one wall-terminating periphery structured and arranged to encompass at least one outer-ear structure adjacent the ear canal. Upon reading the teachings of this specification, those skilled in the art will now appreciate that, under appropriate circumstances, considering issues such as design preference, user preferences, marketing preferences, cost, structural requirements, available materials, technological advances, etc., other suitable dimensions may suffice.

Lip 111 preferably comprises at least one lip aperture 112 structured and arranged to permit the ventilation of air from effluent collector 104. Lip aperture 112 preferably assists to equalize the pressure within cup 124 during use so as to prevent traumatic ear injury, which may be caused by excessive air pressure within effluent collector 104 when pressure is applied to the liquid container and through injector tube 105. Preferably, lip aperture 112 comprises three grooves through the collector lip 111, as shown (see FIG. 5); alternately preferably just one groove. Preferably, each respective lip aperture 112 is rounded and approximately three millimeters in diameter. Upon reading this specification, those skilled in the art will now appreciate that, under appropriate circumstances, considering such issues as design preference, user preferences, marketing preferences, cost, structural requirements, available materials, technological advances, etc., other pressure release arrangements such as, for example, smaller or larger apertures, more or fewer apertures, tubules, slots, perforations, one-way valves, etc., may suffice.

Cylindrical member 125 is preferably integrally connected with effluent collector 104 and cup 124. Cylindrical member 125 (at least herein embodying at least one connector structured and arranged to connect said at least one injector, said at least one collector, and said at least one coupler) preferably rigidly connects with injector nozzle 113. Cylindrical member 125 preferably has an inner bore 131 with internal helical threads 123 and preferably comprises a female coupling 121, as shown. Cylindrical member 125 preferably is open at one end, and preferably is capped by conical-engagement surface 130 at the opposite end, as shown (see particularly FIG. 6). Conical-engagement surface 130 preferably protrudes into the inner bore 131 of cylindrical member 125, as shown. The internal helical threads 123 of female coupling 121 (at least herein embodying said at least one coupler comprising at least one threaded coupler structured and arranged to threadably engage said at least one threaded opening of said at least one liquid container) preferably are formed with a size and pitch providing near "universal" thread compatibility with the external helical threads 122 comprising the male coupling 120 of irrigation bottles in the above-noted range. Effluent collector 104 preferably is designed to fit wide mouth standard irrigation bottles comprising slightly differing bottle end opening configurations. More specifically, effluent collector 104 preferably is designed to fit any of three commercially-available standard wide-mouth standard irrigation pour bottles having an outer neck diameter in the range of about three and one-half centimeters (cm). These preferred products include squeezable standard wide-mouth standard irrigation pour bottles from Baxter Healthcare Corporation of Deerfield Ill., Hospira Worldwide Inc. of Lake Forest Ill., and B. Braun Medical Inc. of Allentown Pa. Internal helical threads 123 preferably have thread dimensions compatible with the above-noted products. Internal helical threads 123 preferably comprise 1-1/2-6 UNC thread dimension. Internal helical threads 123 preferably comprise 1-1/2-6 UNC coarse thread dimension. Preferably, internal helical threads 123 comprise at least two turns, more preferably at least two and one-half turns. Less than two turns increases the likelihood of cross threading problems, and is therefore less preferable. More than two and one-half turns helps prevent cross threading and improves universal sealing to a variety of different sized bottles. Upon reading this specification, those with ordinary skill in the art will now appreciate that, under appropriate circumstances, considering such issues as design preference, user preferences, marketing preferences, cost, structural requirements, available materials, technological advances, etc., other coupling arrangements such as, e.g., bayonet fittings, other threaded fittings, rubber sealing mechanisms, etc., may suffice.

Female coupling 121 preferably is structured and arranged to provide a liquid-tight seal when the female coupling 121 is engaged with the male coupling 120 of an irrigation squeeze bottle 102 such that irrigation liquid 117 can escape only through the tube outlet 110 of injector tube 105 (and liquid cannot escape through the connection, threads, etc.). The above-described arrangement at least herein embodies at least one threaded coupler and the at least one threaded opening, that when tightly engaged, comprise at least one liquid seal structured and arranged to form at least one liquid-resistant seal between at least one standard wide-mouth irrigation pour bottle and said at least one threaded coupler). The inner bore 131 of female coupling 121 preferably is closed at one end by smoothly finished conical-engagement surface 130. A liquid-tight seal preferably is achieved by contact between bottle lip 132 and conical-engagement surface 130, as shown. A liquid-tight seal preferably is achieved by screwing the male coupling 120 of irrigation squeeze bottle 102 into the female coupling 121 of effluent collector 104 (engaging the external helical threads 122 of cylindrical neck 103 with the internal helical threads 123 of cylindrical member 125) until the bottle lip 132 seats tightly on the conical-engagement surface 130.

Conical-engagement surface 130 preferably comprises a hollow truncated cone preferably extending from the preferably closed back of cylindrical member 125 and preferably protruding into the inner bore 131 of cylindrical member 125, as shown. Conical-engagement surface 130 preferably permits a liquid-tight seal preferably without relying on resilient material so that effluent collector 104 can be manufactured from a single molding preferably to reduce costs.

The coarse internal helical threads 123 preferably engage with a variety of types of external helical threads 122 and preferably will bias bottle lip 132 into engagement with conical-engagement surface 130, as shown. The external taper of conical-engagement surface 130 preferably provides a circular engagement surface of increasing radius. When male coupling 120 is screwed into female coupling 121, bottle lip 132 preferably will seat tightly on the portion of the conical-engagement surface 130 comprising a diameter greater or equal to the diameter of the bottle lip 132. In the above-described manner, female coupling 121 can accommodate male couplings of varying diameters and still provide a liquid-tight seal (preventing leaking of liquid) at pressures of at least about four pounds per square inch, preferably remaining liquid-tight at pressures of about seven pounds per square inch. Upon reading this specification, those with ordinary skill in the art will now appreciate that, under appropriate circumstances, considering such issues as design preference, user preferences, marketing preferences, cost, structural requirements, available materials, technological advances, etc., other liquid-tight arrangements such as, e.g., including at least one resilient material, sealing compounds, etc., may suffice.

According to another preferred embodiment of the present invention, nozzle portion 113 preferably is centrally located within the cylindrical member 125 of effluent collector 104. Nozzle portion 113 preferably is integral to conical-engagement surface 130, and preferably comprises a conical surface that is coaxial to conical-engagement surface 130, but that preferably extends from the back surface of cylindrical member 125 away from inner bore 131. The tip of nozzle portion 113 preferably comprises a smoothbore aperture 109. The inner diameter of smoothbore aperture 109 preferably is large enough that a user 114 preferably may insert and adjustably move, e.g., a size French 10 catheter through smoothbore aperture 109 by hand 116. The above-described arrangement at least herein embodies at least one positional support comprising at least one internal bore structured and arranged to permit moveable engagement with said at least one flexible tube. Preferably, the inner diameter of smoothbore aperture 109 is sufficiently narrow so as to provide a friction fit that will prevent a size French 10 catheter from sliding through smoothbore aperture 109 during ordinary use (without user manipulation) Smoothbore aperture 109 preferably has an inner diameter of about three millimeters, more preferably 3.16 millimeters. Upon reading this specification, those with ordinary skill in the art will now appreciate that, under appropriate circumstances, considering such issues as design preference, user preferences, marketing preferences, cost, structural requirements, available materials, technological advances, etc., other bore arrangements such as, e.g., multiple bore, smaller or larger bore, etc., may suffice.

Figure 7:
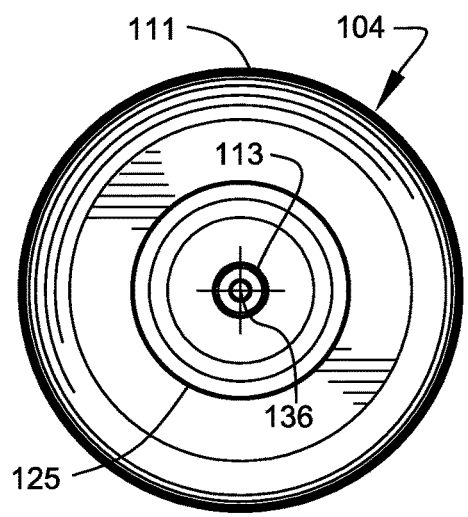
FIG. 7 shows a top view, illustrating a central placement of a cylinder within a drainage collector cup, according to another preferred embodiment of the present invention.
Figure 8:
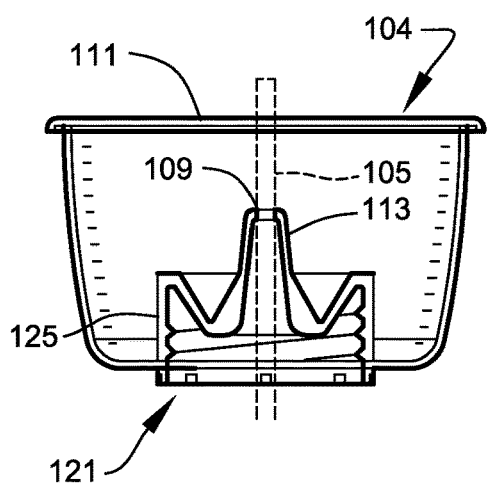
FIG. 8 shows a side view of the drainage collector, according to the preferred embodiment of FIG. 7.

FIG. 7 is top view showing a central placement of a cylinder within an effluent collector 104 according to another preferred embodiment of the present invention. In the alternative embodiment, cylindrical member 125 preferably is centrally located within cup 124 at center 136 (at least herein embodying at least one internal bore is centrally placed relative to said base wall). FIG. 8 is a side view of the effluent collector 104 according to the preferred embodiment of FIG. 7. FIG. 8 preferably illustrates a central placement of cylindrical member 125 within cup 124, as shown.

Figure 9:
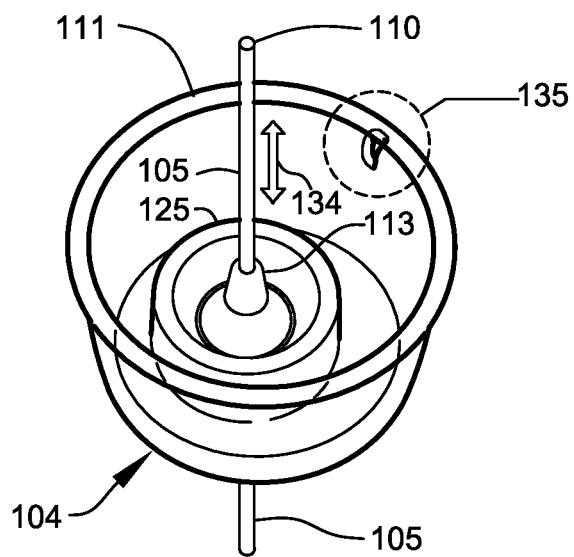
FIG. 9 shows a perspective view of a lip aperture, according to a preferred embodiment of the present invention.
Figure 10:
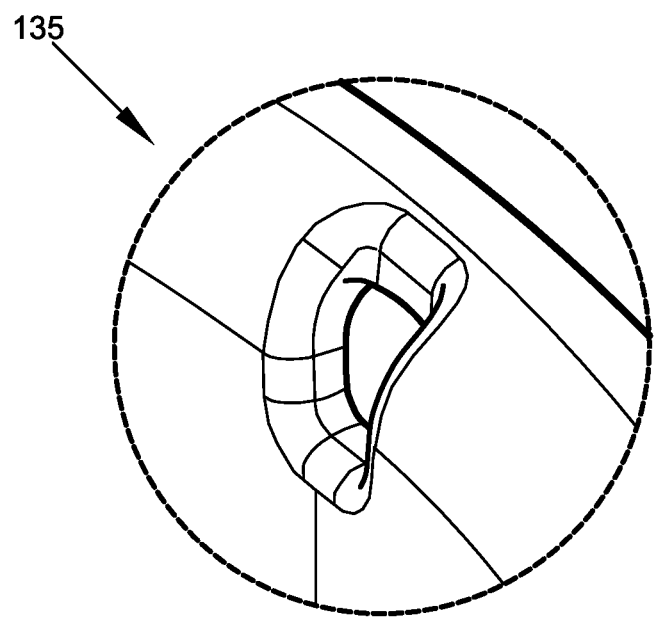
FIG. 10 shows an enlarged detail view of Detail 135 of FIG. 9.

FIG. 9 is a perspective view of a lip aperture according to a preferred embodiment of the present invention. FIG. 10 is an enlarged detail view of Detail 135 of FIG. 9. FIG. 9 preferably depicts an alternate embodiment of the lip aperture of effluent collector 104. The alternative lip apertures comprise exactly one aperture 135 that is located slightly beneath the lip of cup 124, as shown. FIG. 10 is a close-up view illustrating alternative lip aperture 135 according to the preferred embodiment of FIG. 9.

Alternative lip aperture 135 preferably comprises at least one ventilation aperture to prevent traumatic ear injury caused by excessive pressure within effluent collector 104 (at least herein embodying at least one collector comprising at least one distal aperture structured and arranged to assist preventing of harmful pressure differentials when irrigating the ear canal). Alternative lip aperture 135 preferably equalizes the air pressure within cup 124 during ordinary use. During ordinary use, cup 124 preferably is oriented such that alternative lip aperture 135 is facing upward. If alternative lip aperture 135 is facing upward during use, excessive air pressure will vent through alternative lip aperture 135 while liquid-containing effluent 118 collects in cup 124. Upon reading this specification, those with ordinary skill in the art will now appreciate that, under appropriate circumstances, considering such issues as design preference, user preferences, marketing preferences, cost, structural requirements, available materials, technological advances, etc., other aperture arrangements such as, e.g., perforations, slots, etc., may suffice.

Figure 11:
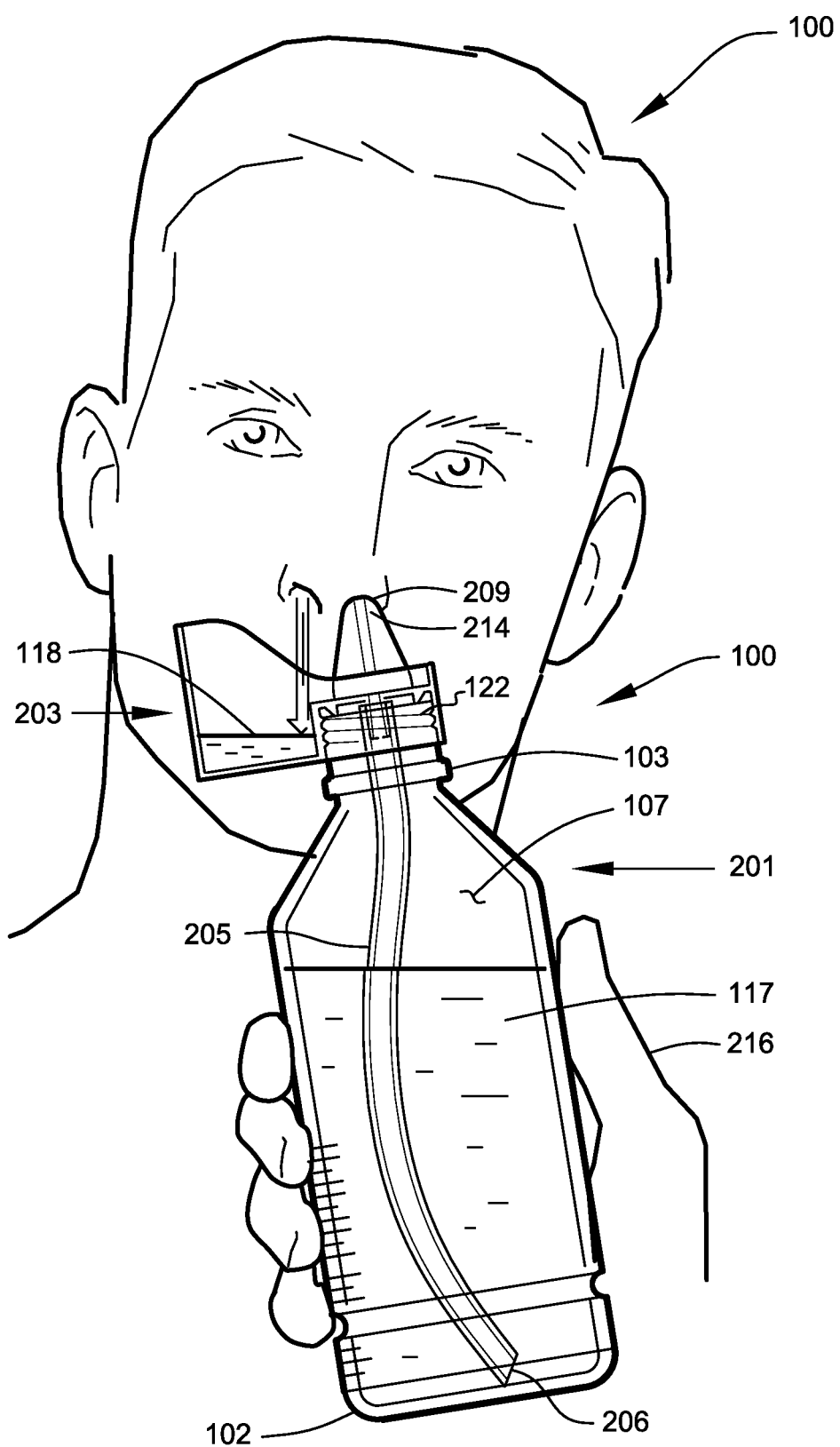
FIG. 11 shows a perspective view, illustrating the use of an assembled nasal irrigator of the otorhinologic irrigation system, according to an alternate preferred embodiment of the present invention.

FIG. 11 shows a perspective view illustrating the use of a preferred nasal-irrigation embodiment of the otorhinologic irrigation system 100 identified herein as nasal irrigator assembly 201. Generally stated, nasal irrigator assembly 201 preferably comprises a nasal irrigator 203 removably attached to an irrigation squeeze bottle 102, as shown. It should be noted that irrigation squeeze bottle 102 (at least embodying herein at least one liquid container comprising at least one manually-deformable internal reservoir structured and arranged to contain a volume of such liquid) preferably comprises one of the previously-described standard commercial wide-mouth irrigation pour bottles. Preferred embodiments of the present system comprise only nasal irrigator 203. Alternately preferably, preferred embodiments of the present system are supplied with both nasal irrigator 203 and irrigation squeeze bottle 102. Furthermore, alternate preferred embodiments of the present system include irrigation squeeze bottles 102 having a prefilled volume of irrigation liquid 117.

Figure 12:
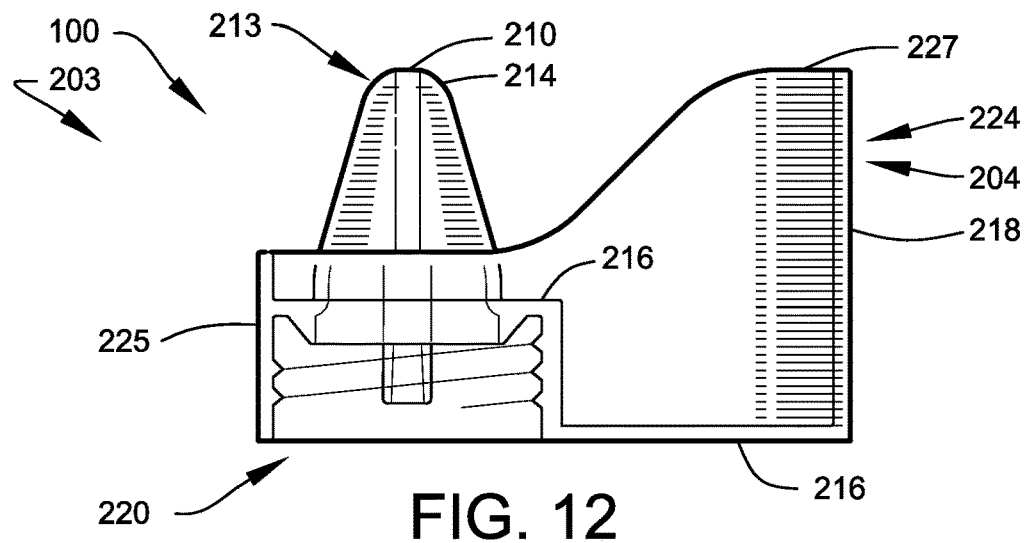
FIG. 12 shows a side view of the nasal irrigator, according to the preferred embodiment of FIG. 11.

FIG. 12 shows a side view of the preferred nasal irrigator 203 of FIG. 11. The primary structures of nasal irrigator 203 preferably consist of a liquid-injecting nozzle portion 213, effluent collector 204, and coupler 220 to enable coupling of the device to irrigation squeeze bottle 102, as shown in FIG. 11. Nasal irrigator 203 is also preferably configured to be coupled to a dip tube 205 situated within the deformable internal reservoir 107 of irrigation squeeze bottle 102, as shown in FIG. 11 and later in FIG. 16. When nasal irrigator 203 and irrigation squeeze bottle 102 are joined, dip tube 205 preferably extends downwardly from nasal irrigator 203 to terminate at a tube inlet 206 located near the base of irrigation squeeze bottle 102 (such dip tube 205 at least embodying herein at least one liquid transport tube configured to assist transporting such liquid from at least one bottom interior portion of such at least one manually-deformable internal reservoir).

Nozzle portion 213 preferably functions to facilitate the injection of irrigation liquid 117 into one or more otorhinologic structures of the patient's head (at least embodying herein at least one liquid injector structured and arranged to assist injection of the liquid into an otorhinologic structure of the head). In the present preferred embodiment, the nozzle preferably functions to administer a sterile liquid saline solution into the patient's nasal passages and sinus cavity.

The preferred shape configuration of nozzle portion 213 is preferably that of a rounded bulb 214 with a generally frustoconical base, as shown. Nozzle portion 213 is preferably configured to form a seal with the patient's nostril 209 during treatment (see FIG. 11). Thus, nasal bulb 214 preferably functions as an anatomical adapter to adapt the liquid-injecting structures of the apparatus to the anatomical geometries of the target otorhinologic structures of the patient's head.

Nasal irrigator 203 is preferably configured such that irrigation liquid 117 exits the distal end of nozzle portion 213 through a discharge port 210, as shown. As will be discussed in greater detail below, discharge port 210 is in fluid communication with the manually-deformable internal reservoir of irrigation squeeze bottle 102.

Figure 13:
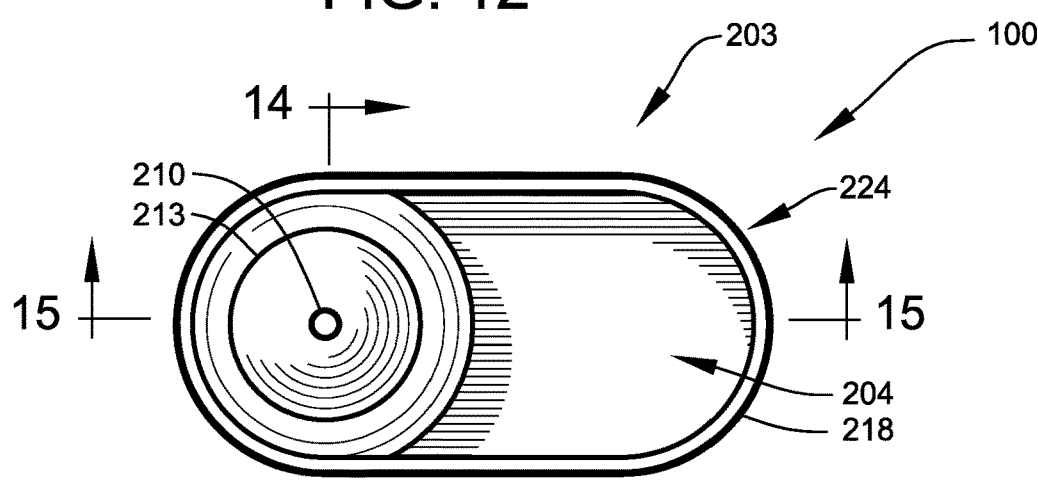
FIG. 13 shows a top view illustrating the nasal irrigator of FIG. 11.

FIG. 13 shows a top view illustrating nasal irrigator 203 of FIG. 11. In reference to both FIG. 11 and FIG. 12, the cup-shaped member 224 forming effluent collector 204 preferably comprises a stepped base wall 216 and a continuous surrounding wall 218 projecting outwardly from the periphery of base wall 216, as shown.

In the preferred arrangements of the present preferred embodiment, surrounding wall 218 comprises a stadium-shaped configuration having two opposing semicircular ends joined tangentially by a pair of straight sides, as shown. Nozzle portion 213 is preferably situated within surrounding wall 218 and is fully surrounded by the liquid-containment structures forming effluent collector 204, as shown. Nozzle portion 213 preferably projects outwardly from of upper step of base wall 216 to pass through effluent collector 204, thereby placing discharge port 210 distal of base wall 216 and in a preferred position beyond the adjacent surrounding wall 218, as shown.

The preferred asymmetrical nozzle placement within effluent collector 204 facilitates the efficient collection and retention of the liquid-containing effluent 118 by placing the deepest region of the open cup-shaped member 224 generally below the open nostril 209 through which the liquid-containing effluent 118 exits (see FIG. 11). Preferably, the upwardly-sweeping periphery of surrounding wall 218 accommodates the anatomical structures of the head while generating an elevated splash shield 227 to assist in preventing splashing of liquid-containing effluent 118 beyond the effluent collector.

Figures 14, 15:
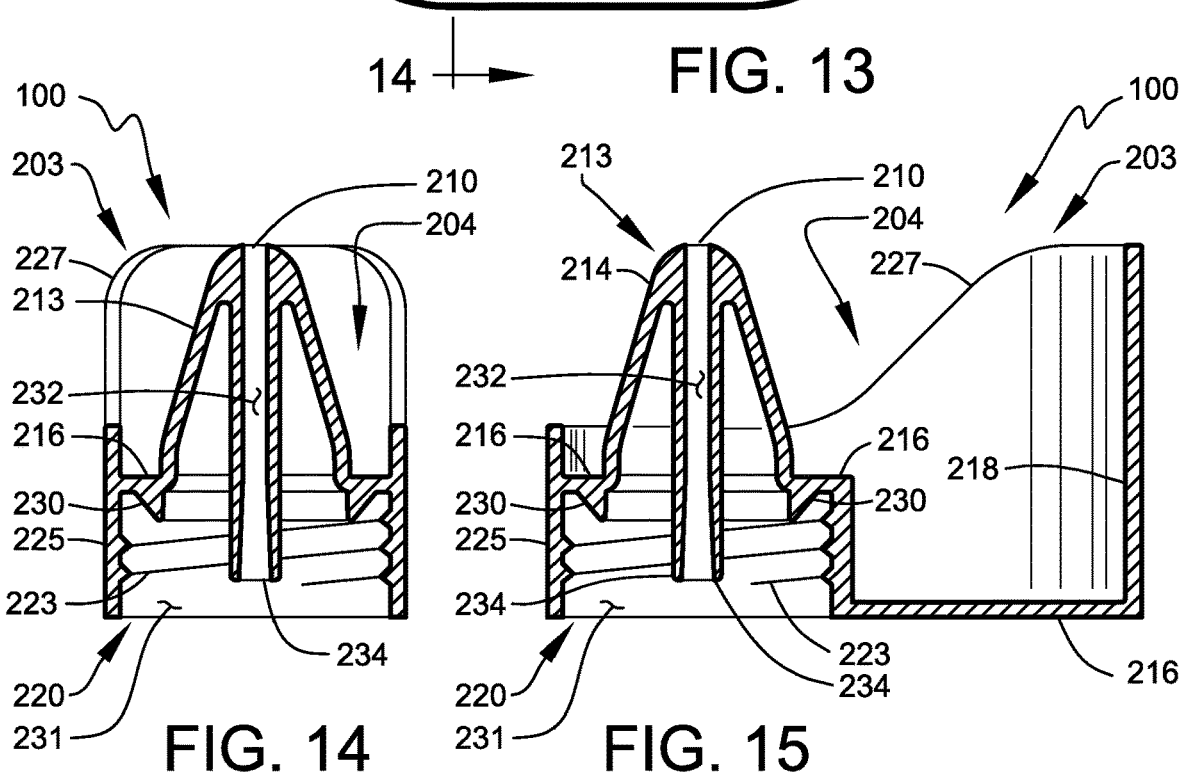
FIG. 14 shows a sectional view through section 14-14 of FIG. 13.
FIG. 15 shows a sectional view through section 15-15 of FIG. 13.

Referring to the sectional views of FIG. 14 and FIG. 15, nasal irrigator 203 preferably comprises coupler 220 to enable the removable coupling of the apparatus to the irrigation squeeze bottle 102 shown in FIG. 11. In a preferred arrangement, coupler 220 comprises a threaded an internally-threaded coupler 220 configured to threadably engage the external helical threads 122 formed within the cylindrical neck 103 of irrigation squeeze bottle 102. As in the prior-described embodiments, a preferred coupler configuration comprises a cylindrical member 225 having an inner bore 231 containing a set of helical threads 223, as shown. The lower end of inner bore 231 is preferably open, as shown, to allow the neck of the bottle to pass within cylindrical member 225 to engage the threads. The upper portion of the cylindrical member is preferably is capped by the upper stepped portion of base wall 216, as shown. Preferably, a conical-engagement surface 230 projects from the upper stepped portion of base wall 216 downwardly into inner bore 231, as shown. The internal helical threads 223 of coupler 220 are preferably formed with a size and pitch providing near "universal" thread compatibility with the external helical threads 122 of irrigation bottles in the previously-noted range. Coupler 220 is preferably designed to fit wide mouth standard irrigation bottles comprising slightly differing bottle end opening configurations.

Coupler 220 is preferably configured to provide a liquid-tight seal when engaged with the irrigation squeeze bottle 102 such that irrigation liquid 117 can escape only through discharge port 210 and liquid cannot escape through the connection, threads, etc. A liquid-tight seal preferably is achieved by contact between bottle lip 132 (see FIG. 2B) and smooth conical-engagement surface 230. A liquid-tight seal preferably is achieved by screwing the male coupling 120 of irrigation squeeze bottle 102 into coupler 220, thereby engaging the external helical threads 122 of cylindrical neck 103 with the internal helical threads 223 of cylindrical member 225 until the bottle lip 132 seats tightly on the conical-engagement surface 230 (at least embodying herein wherein such at least one threaded coupler and the at least one threaded opening, when tightly engaged, comprise at least one liquid seal structured and arranged to form at least one liquid-resistant seal between such at least manually-deformable internal reservoir of such at least one standard wide-mouth irrigation pour bottle and such at least one threaded coupler). Upon reading the teachings of this specification, those skilled in the art will now appreciate that, under appropriate circumstances, considering such issues as design preference, user preferences, marketing preferences, cost, structural requirements, available materials, technological advances, etc., other coupling arrangements such as, for example, bayonet fittings, other threaded fittings, rubber sealing mechanisms, etc., may suffice.

A liquid transport channel 232 is formed within nozzle portion 213 to transport irrigation liquid 117 between the manually-deformable internal reservoir 107 and discharge port 210. The lower end of liquid transport channel 232 preferably comprises a transport-tube coupler 234 configured to removably couple liquid transport channel 232 to dip tube 205, as illustrated in FIG. 16.

Figures 16, 17, 18:
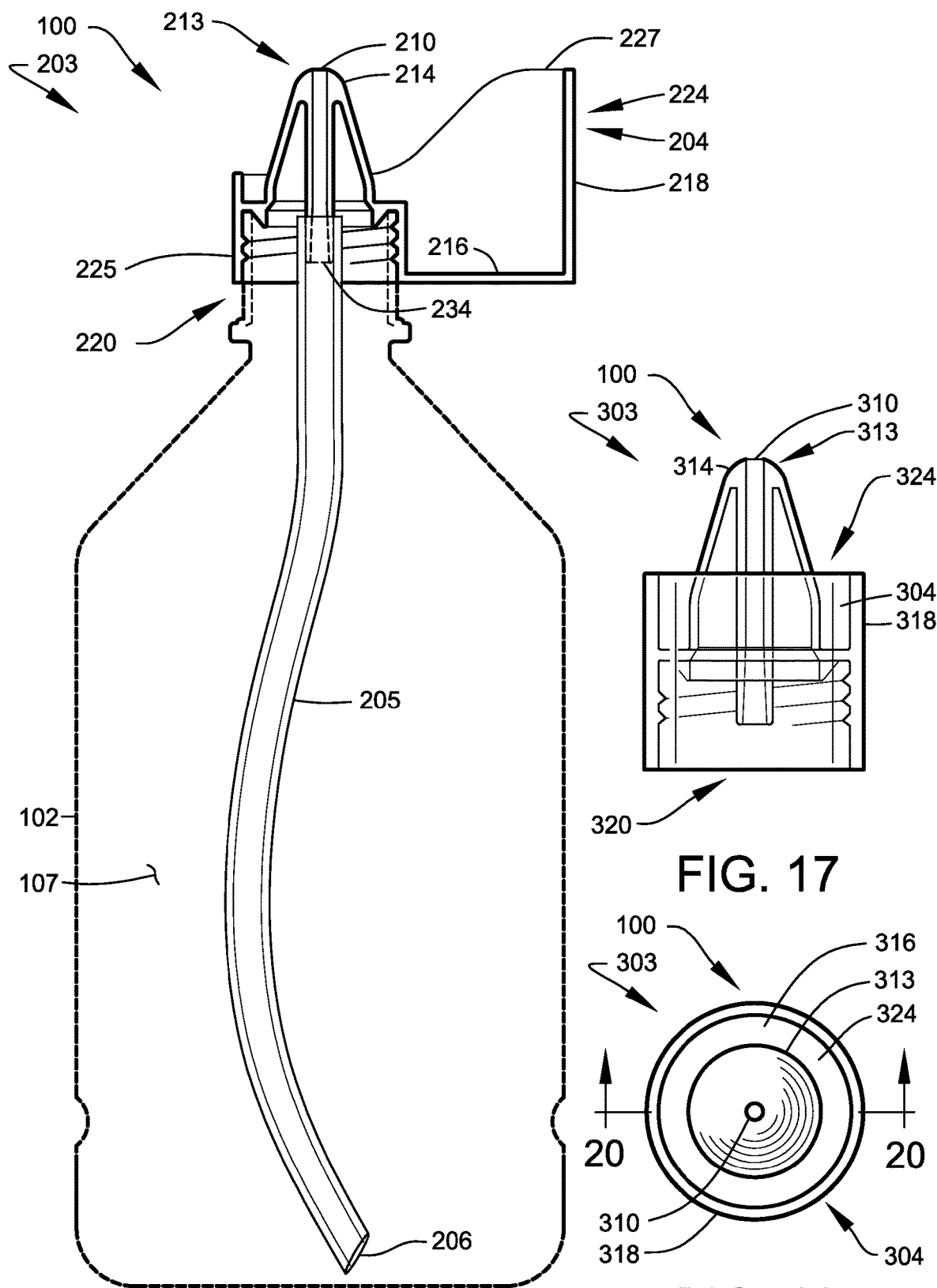
FIG. 16 shows a sectional view, diagrammatically illustrating the nasal irrigator fitted with a dip tube and coupled to a liquid container, according to the preferred embodiment of FIG. 11.
FIG. 17 shows a side view, of an alternate nasal irrigator, an alternate preferred embodiment of the present invention.
FIG. 18 shows a top view illustrating the alternate nasal irrigator of FIG. 16.

FIG. 16 shows a sectional view, diagrammatically illustrating nasal irrigator 203 fitted with a dip tube 205 and coupled to irrigation squeeze bottle 102, according to the preferred embodiment of FIG. 11. Transport-tube coupler 234 preferably comprises a hollow cylindrical extension of liquid transport channel 232, as shown. Dip tube 205 is preferably engaged on transport-tube coupler 234 by sliding the inner bore of dip tube 205 over the outer circumferential surface of the coupler, as shown.

Dip tube 205 preferably functions to transport irrigation liquid 117 from the bottom interior portion of manually-deformable internal reservoir 107 upwardly to liquid transport channel 232. When assembled, volumetric reductions of the manually-deformable internal reservoir 107, by manual deformation of outer wall 126, assists injection of irrigation liquid 117 from nozzle portion 213. Upon reading the teachings of this specification, those skilled in the art will now appreciate that, under appropriate circumstances, considering such issues as design preference, user preferences, medical needs, marketing preferences, cost, structural requirements, available materials, technological advances, etc., other discharge methods, such as, for example, manual or electrical pumping, etc., may suffice.

The above-described structures of nasal irrigator 203 are preferably connectively unified into a single monolithic body, as shown. Nasal irrigator 203 is preferably formed from a single durable and substantially rigid material capable of maintaining nozzle portion 213, effluent collector 204, and coupler 220 in a defined geometric relationship (at least embodying herein at least one unifying connector structured and arranged to connect such at least one liquid injector, such at least one effluent collector, and such at least one coupler). Nasal irrigator 203 is preferably constructed of a single molded plastic. Preferred plastics comprise medical-grade polymers having a durometer shore hardness of about 75D. Preferred plastics may include transparent polymer so as to provide a view of the liquid-containing effluent 118 while it is collected within effluent collector 204.

In ordinary use, a user 114 preferably gently inserts bulb 214 of nozzle portion 213 within one nostril 209 while simultaneously placing the open end of effluent collector 204 below the open nostril 209, as generally illustrated in FIG. 11. With bulb 214 forming a liquid seal with the nostril 209, user 114 preferably gently squeezes irrigation squeeze bottle 102 to initiate the flow of irrigation liquid 117. Squeezing irrigation squeeze bottle 102 preferably deforms the outer wall 126 of irrigation squeeze bottle 102 so as to reduce the internal volume of the manually-deformable internal reservoir 107. Deforming outer wall 126 increases the pressure on irrigation liquid 117 contained within the manually-deformable internal reservoir 107, thus forcing the irrigation liquid 117 into tube inlet 206, through dip tube 205, and out discharge port 210 into the user's nasal passage and sinus cavity.

Liquid-containing effluent 118 draining from the opposing nostril 209 is preferably captured by effluent collector 204 which also acts as splash shield to prevent the effluent from splashing beyond the surrounding wall 218, as shown. In some preferred embodiments of the system, effluent collector 204 is preferably transparent so as to permit a physician to examine of the collected liquid-containing effluent 118 before being discarded.

FIG. 17 shows a side view of an alternate nasal irrigator 303 of otorhinologic irrigation system 100. The principal preferred structures of alternate nasal irrigator 303 consist of a liquid-injecting nozzle portion 313, a compact, symmetrically-shaped, effluent collector 304, and a threaded coupler 320, as shown. Nozzle portion 313 preferably functions to facilitate the injection of irrigation liquid 117 into one or more otorhinologic structures of the patient's head (at least embodying herein at least one liquid injector structured and arranged to assist injection of the liquid into an otorhinologic structure of the head). In the present alternate embodiment, nozzle portion 313 preferably functions to administer a sterile liquid saline solution into the patient's nasal passages and sinus cavity. The preferred shape configuration of nozzle portion 313 is preferably that of a rounded bulb 314 with a frustoconical base. Nozzle portion 313 is preferably configured to form a seal with the patient's nostril 209 during treatment (see the similar illustration of FIG. 11). Thus, nasal bulb 314 preferably functions as an anatomical adapter to adapt the liquid-injecting structures of the apparatus to the anatomical geometries of the target otorhinologic structures of the patient's head.

The apparatus is preferably configured such that irrigation liquid 117 exits the distal end of nozzle portion 313 through a discharge port 310. When alternate nasal irrigator 303 is coupled with irrigation squeeze bottle 102, discharge port 310 is preferably in fluid communication with the manually-deformable internal reservoir within irrigation squeeze bottle 102.

FIG. 18 shows a top view illustrating alternate nasal irrigator 303 of FIG. 16. In reference to both FIG. 17 and FIG. 18, the cup-shaped member 324 forming effluent collector 304 preferably comprises a base wall 316 and a continuous surrounding wall 318 projecting outwardly from the circumferential periphery of base wall 316, as shown.

In the preferred arrangements of the present preferred embodiment, surrounding wall 318 comprises a substantially cylindrical configuration, as shown. Nozzle portion 313 is preferably situated centrally within surrounding wall 318 and is fully surrounded by the liquid-containment structures forming effluent collector 304, as shown. Nozzle portion 313 preferably projects outwardly from base wall 316 to pass through the upper opening of effluent collector 304 thereby placing discharge port 310 distal of base wall 316 and in a preferred position beyond the adjacent surrounding wall 318, as shown.

The preferred symmetrical nozzle placement within effluent collector 304 preferably allows the open cup-shaped member 324 to be situated closely adjacent the face of the user. Preferably, the elevated surrounding wall 318 generates a splash shield 327 to assist in preventing splashing of liquid-containing effluent beyond the confines of the effluent collector.

Figure 19:
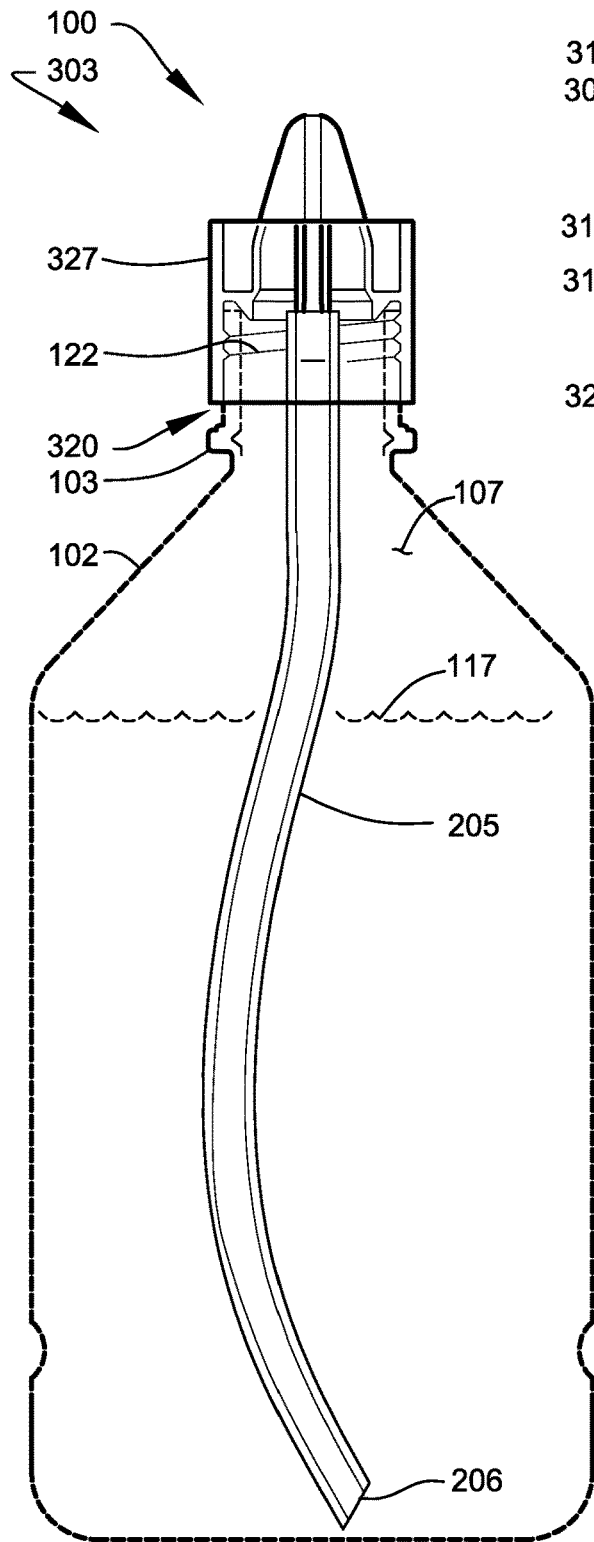
FIG. 19 shows a sectional view diagrammatically illustrating the alternate nasal irrigator, fitted with a dip tube and coupled to a liquid container, according to the preferred embodiment of FIG. 11.
Figure 20:
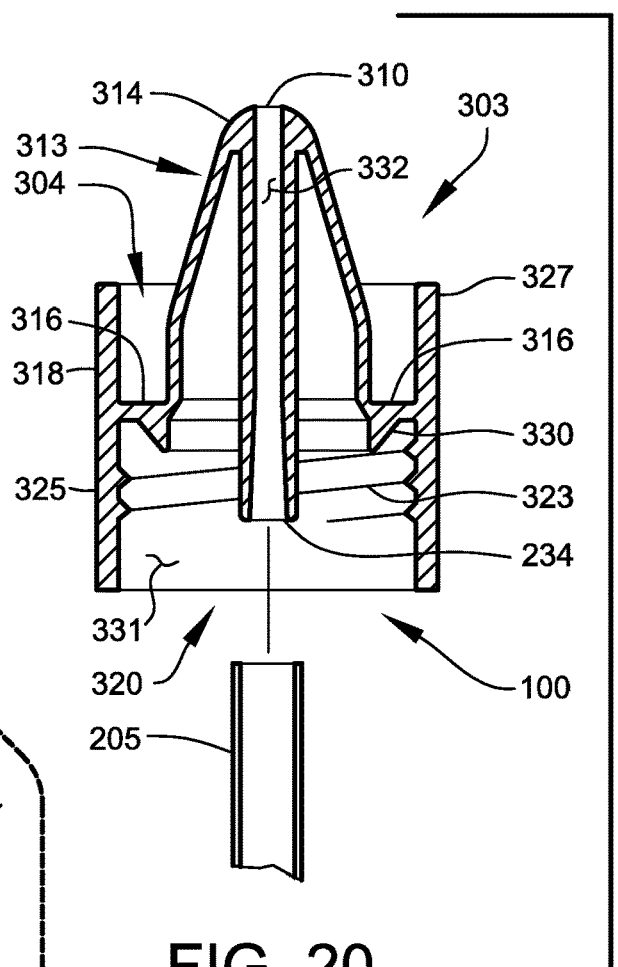
FIG. 20 shows an exploded sectional view through section 20-20 of FIG. 18.
Figure 21:
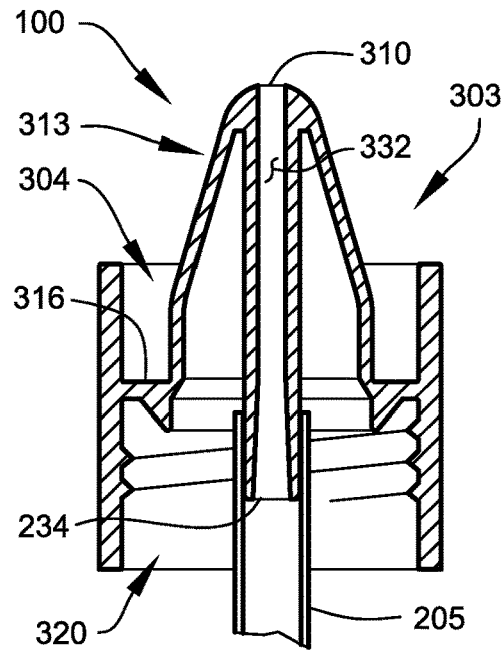
FIG. 21 shows a sectional view, through section 20-20 of FIG. 18, illustrating the alternate nasal irrigator of FIG. 17 fitted with a dip tube.

Referring to the sectional view of FIG. 20 and FIG. 21, alternate nasal irrigator 303 preferably comprises one or more physical structures enabling the removable coupling of the apparatus to the irrigation squeeze bottle 102 shown in FIG. 19. In a preferred arrangement, threaded coupler 320 is preferably configured to threadably engage the external helical threads 122 formed within the cylindrical neck 103 of irrigation squeeze bottle 102 is formed within the base of effluent collector 304. As in the prior embodiments, a preferred coupler configuration comprises a cylindrical member 325, as shown. In the present preferred embodiment of the system, the cylindrical surrounding wall 318 of effluent collector 304 extends downwardly (past base wall 316) to form cylindrical member 325, as shown.

Preferably, the hollow cylindrical member 325 comprises an inner bore 331 that preferably contains a set of helical threads 323, as shown. The lower end of inner bore 331 is preferably open, as shown, to allow the neck of the bottle to pass within cylindrical member 325 to engage the threads. The upper portion of inner bore 331 is preferably is capped by base wall 316, as shown. Preferably, a conical-engagement surface 330 projects from the upper stepped portion of base wall 316 downwardly into inner bore 331, as shown. As in the prior embodiments, the internal helical threads 323 of coupler 320 are preferably formed with a size and pitch providing near "universal" thread compatibility with the external helical threads 122 of irrigation bottles in the previously-noted range. Thus, coupler 320 is preferably designed to fit wide mouth standard irrigation bottles comprising slightly differing bottle end opening configurations.

Coupler 320 is preferably configured to provide a liquid-tight seal when engaged with the irrigation squeeze bottle 102 such that irrigation liquid 117 can escape only through discharge port 310 and liquid cannot escape through the connection, threads, etc. A liquid-tight seal preferably is achieved by contact between bottle lip 132 (see FIG. 2B) and the smooth conical-engagement surface 330. A liquid-tight seal preferably is achieved by screwing the male coupling 120 of irrigation squeeze bottle 102 into coupler 320, thereby engaging the external helical threads 122 of cylindrical neck 103 with the internal helical threads 323 of cylindrical member 325 until the bottle lip 132 seats tightly on the conical-engagement surface 330 (at least embodying herein wherein such at least one threaded coupler and the at least one threaded opening, when tightly engaged, comprise at least one liquid seal structured and arranged to form at least one liquid-resistant seal between such at least manually-deformable internal reservoir of such at least one standard wide-mouth irrigation pour bottle and such at least one threaded coupler).

A liquid transport channel 332 formed within nozzle portion 313 is preferably used to transport irrigation liquid 117 between the manually-deformable internal reservoir 107 and discharge port 310. The lower end of liquid transport channel 332 preferably comprises the transport-tube coupler 234 of the prior-described embodiment. Transport-tube coupler 234 is preferably configured to removably couple the internal liquid transport channel 332 to dip tube 205, as generally illustrated in FIG. 19.

FIG. 19 shows a sectional view diagrammatically illustrating alternate nasal irrigator 303, fitted with a dip tube 205 and coupled to a liquid container, according to the preferred embodiment of FIG. 17. As in the prior-described embodiment, when alternate nasal irrigator 303 and irrigation squeeze bottle 102 are joined, dip tube 305 preferably extends downwardly from alternate nasal irrigator 303 to terminate at tube inlet 206 located near the base of irrigation squeeze bottle 102.

Transport-tube coupler 234 preferably comprises a hollow cylindrical extension of liquid transport channel 332, as shown. Dip tube 205 is preferably engaged on transport-tube coupler 234 by sliding the inner bore of dip tube 205 over the outer circumferential surface of the coupler, as shown.

Dip tube 205 preferably functions to transport irrigation liquid 117 from the bottom interior portion of manually-deformable internal reservoir 107 to upwardly to liquid transport channel 332. When assembled, volumetric reductions of the manually-deformable internal reservoir 107, by manual deformation of outer wall 126, assists injection of irrigation liquid 117 from nozzle portion 313.

As with the prior-described embodiment, the structures of alternate nasal irrigator 303 are preferably interconnected within a single monolithic body, as shown. Alternate nasal irrigator 303 is preferably formed from a single durable and substantially rigid material capable of maintaining nozzle portion 313, effluent collector 304, and coupler 320 in a defined geometric relationship (at least embodying herein at least one unifying connector structured and arranged to connect such at least one liquid injector, such at least one effluent collector, and such at least one coupler). Alternate nasal irrigator 303 is preferably constructed of a single molded plastic. Preferred plastics comprise medical-grade polymers having a durometer shore hardness of about 75D. Preferred plastics may include transparent polymer so as to provide a view of the liquid-containing effluent 118 while it is collected within effluent collector 304.

FIG. 22 shows an exploded view, in partial section, illustrating diagrammatically, the coupling of a preferred embodiment of the present invention to one of several liquid-supply sources 400. Preferably, transport-tube coupler 234 further comprises at least one alternate liquid-source coupler 434, as shown.

In one preferred embodiment of the system, alternate liquid-source coupler 434 is configured to couple with a medical syringe 170, as shown. Medical syringe 170 is preferably used to dispense irrigation liquid 117 into the fluid transporting structures of a respective nozzle portion. In a preferred embodiment of the system, alternate liquid-source coupler 434 is configured to receive the specific frustoconical shape of a Luer-type connector 163. In this preferred arrangement, Luer-type connector 163 is located at the distal hub of medical syringe 170, as shown. Upon reading this specification, those with ordinary skill in the art will now appreciate that, under appropriate circumstances, considering such issues as cost, user preference, etc., the use of other fluid sources having Luer-type connectors such as, e.g., flexible I.V. bags, etc., may suffice.

Furthermore, preferred embodiments of alternate liquid-source coupler 434 are configured to accommodate engagement with a specific Luer-connector type, as shown. In one preferred embodiment, the interior bore of transport-tube coupler 234 comprises a Luer taper, preferably a female taper generally matching standard 594 of the International Organization for Standardization (ISO). As shown in FIG. 22, alternate liquid-source coupler 434 is preferably configured to removably connect the irrigation device with medical syringes 170 having either a Luer-Lock connector 171 or a Luer-slip-type connector 172. FIG. 23 shows a side view illustrating the coupling of a preferred embodiment of the present invention to medical syringe 170 having a Luer-slip-type connector 172. Upon reading the teachings of this specification, those of ordinary skill in the art will now understand that, under appropriate circumstances, considering such issues as leakage prevention, then-available technology, etc., other types of syringe connectors to connect with syringe tip receiver, such as, e.g., alternately-gendered fittings, catheter-tip syringes, as-of-yet developed fittings, etc., may suffice.

FIG. 24 shows a side view of alternate nasal irrigator 403 of the present invention. FIG. 25 shows a side view of alternate nasal irrigator 404 of the present invention. Alternate nasal irrigator 403 and alternate nasal irrigator 404 illustrate preferred variations within the physical configurations of the effluent collecting structures. Upon reading this specification, those with ordinary skill in the art will now appreciate that, under appropriate circumstances, considering such issues as design preference, user preferences, marketing preferences, cost, intended use, etc., other effluent collecting arrangements such as, e.g., effluent collecting structures having larger or smaller liquid-retention capacities, alternate splash-shield configurations, alternate peripheral shapes, etc., may suffice.

FIG. 26 shows an exploded view, illustrating a nasal effluent collector 501 attachable to a nasal irrigation bottle 502 of an existing nasal irrigator 504, according to another preferred embodiment of the present invention. FIG. 27 shows a top view illustrating the nasal effluent collector 501 of FIG. 26. Nasal effluent collector 501 is preferably configured to modify existing nasal irrigator 504 through the addition of an attachable nasal effluent collector 501, as shown. Nasal irrigation bottle 502 of existing nasal irrigator 504 preferably comprises flexible sidewalls 506 and a bottle-neck portion 508 having an upper opening 510, as shown. Existing nasal irrigator 504 further comprises a removable cap 512 having a nasal-engaging opening at the cap's uppermost surface. The nasal-engaging opening is configured to be in fluid communication with an interior portion of nasal irrigation bottle 502. Existing nasal irrigators 504 of this type are described in, e.g., U.S. Pat. No. 6,520,384 to Mehta, referenced herein as an example of an implemented apparatus. Commercially available nasal irrigators of this type are supplied by NeilMed Pharmaceuticals Inc. of Houston, Tex.

Nasal effluent collector 501 preferably comprises a generally cup-shaped member 520 configured to collect effluent draining from the nasal passage during an irrigation procedure. The cup-shaped member 520 preferably comprises a base wall 522 and a continuous surrounding wall 524 projecting outwardly from the periphery of base wall 522, as shown. Nasal effluent collector 501 preferably comprises at least one coupler 526 designed to assist the coupling of nasal effluent collector 501 to existing nasal irrigator 504. Coupler 526 preferably comprises aperture opening 528 located within base wall 522, as shown.

FIG. 28 shows a side view, illustrating nasal effluent collector 501 attached in an operable position to existing nasal irrigation bottle 504 of FIG. 26. Aperture opening 528 preferably comprises a size and shape that permits nasal effluent collector 501 to be engaged on bottle-neck portion 508, as shown. In a preferred arrangement, cap 512 is removed and bottle-neck portion 508 is passed through aperture opening 528 until the shoulder of bottle-neck portion 508 is resting on base wall 522 of nasal effluent collector 501. Nasal effluent collector 501 is preferably held to nasal irrigation bottle 504 by securing removable cap 512 over upper opening 510 thereby capturing the portion 527 of base wall 522 peripherally adjacent aperture opening 528, as shown in FIG. 28 (at least embodying herein wherein such at least one effluent collector, when coupled with the bottle, is retained to the bottle-neck opening by the removable cap).

During use, liquid-containing effluent 118 is preferably captured by effluent collector 501, which also acts as splash shield to prevent the effluent from splashing beyond the surrounding wall 524, as shown.

FIG. 29 shows a perspective view, illustrating nasal irrigation adapter 601, according to another preferred embodiment of the present invention. Nasal irrigation adapter 601 is preferably configured to be attachable to a multipurpose medical-irrigation device 602, as shown in FIG. 30. FIG. 30 shows an exploded side view, in partial section, illustrating nasal irrigation adapter 601 and preferred associated components including dip tube 205. FIG. 31 shows a side view, in partial section, illustrating the nasal irrigation adapter 601 and associated components in an assembled configuration.

Nasal irrigation adapter 601 preferably comprises an otorhinologic adapter designed to adapt a multipurpose medical-irrigation device 602 to one or more otorhinologic irrigation functions. In the depicted embodiment, nasal irrigation adapter 601 comprises a nasal bulb 604 configured to sealingly engage a nostril 209 of a patient's nasal passage.

Applicant's multipurpose medical-irrigation device 602 comprises a liquid-injecting nozzle portion 613 and a compact, symmetrically-shaped, effluent collector 614, as shown. Nozzle portion 613 preferably functions to facilitate the injection of irrigation liquid 117 into one or more otorhinologic structures of the patient's head (at least embodying herein at least one liquid injector structured and arranged to assist injection of the liquid into an otorhinologic structure of the head). In addition, the nozzle portion is preferably configured to permit the administration of a sterile liquid saline solution to a wound.

Nasal bulb 604 preferably comprises a shaped internal bore 606 that preferably extends through the center of the adapter to terminate at an upper discharge port 608, as shown. Internal bore 606 is preferably configured to engage the projecting liquid-injecting nozzle portion 613. When so engaged, irrigation liquid 117 exiting liquid-injecting nozzle portion 613 is transported through internal bore 606 to exit discharge port 608.

Nasal bulb 604 is preferably constructed from a non-toxic material suitable for medical use. In one preferred configuration, nasal bulb 604 preferably comprises a semi-resilient material. Alternately preferably, nasal bulb 604 comprises a substantially rigid material.

Figure 32:
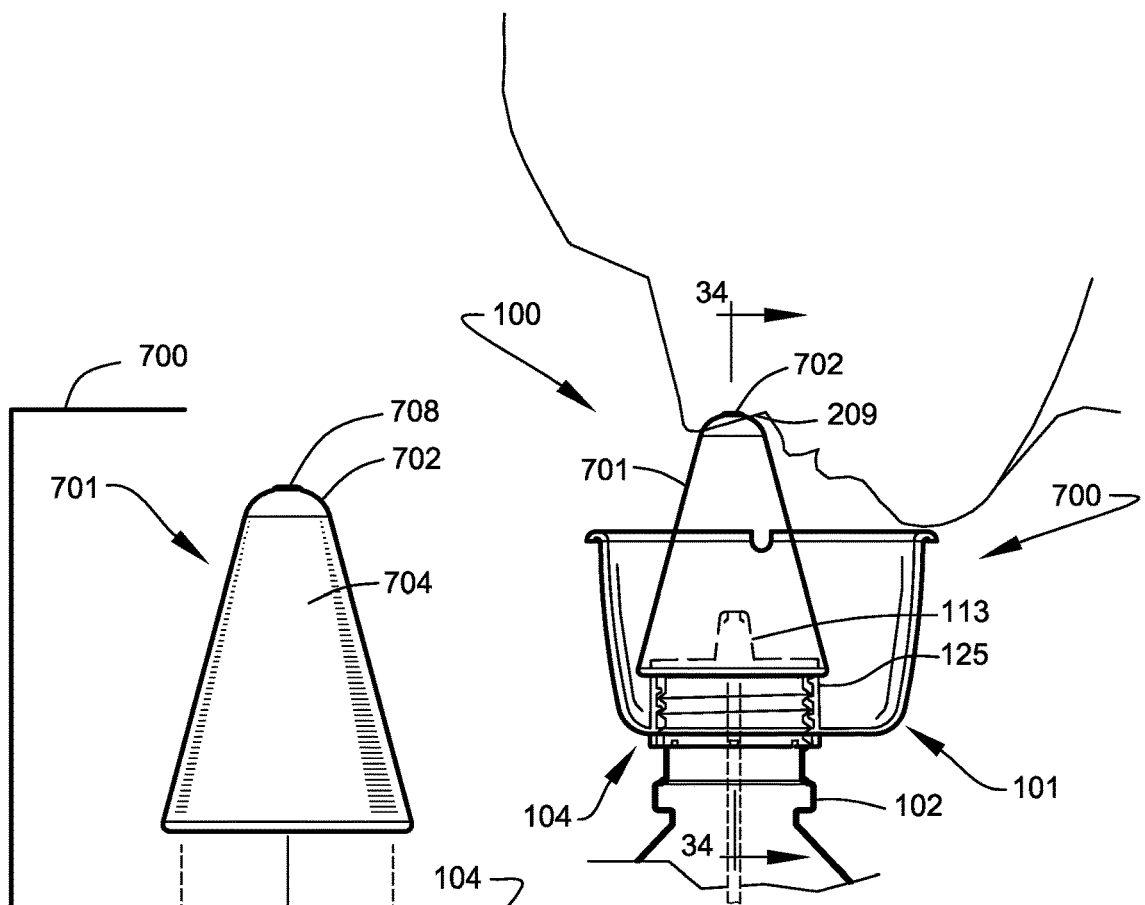
FIG. 32 shows a perspective view, illustrating the use of an alternate nasal irrigator of the otorhinologic irrigation system, according to another preferred embodiment of the present invention.

FIG. 32 shows a perspective view, illustrating the use of an alternate nasal irrigator 700 of otorhinologic irrigation system 100, according to another preferred embodiment of the present invention. Preferably, alternate nasal irrigator 700 utilizes a specialized nasal irrigation adapter 701 configured to adapt ear irrigator 101, of FIG. 1A, to a nasal irrigation function, as shown. In the depicted embodiment, nasal irrigation adapter 701 comprises an attachable cone-shaped member having a blunt end bulb 702 configured to project outwardly from collector 104 to sealingly engage a nostril 209 of a patient's nasal passage.

Figure 33:
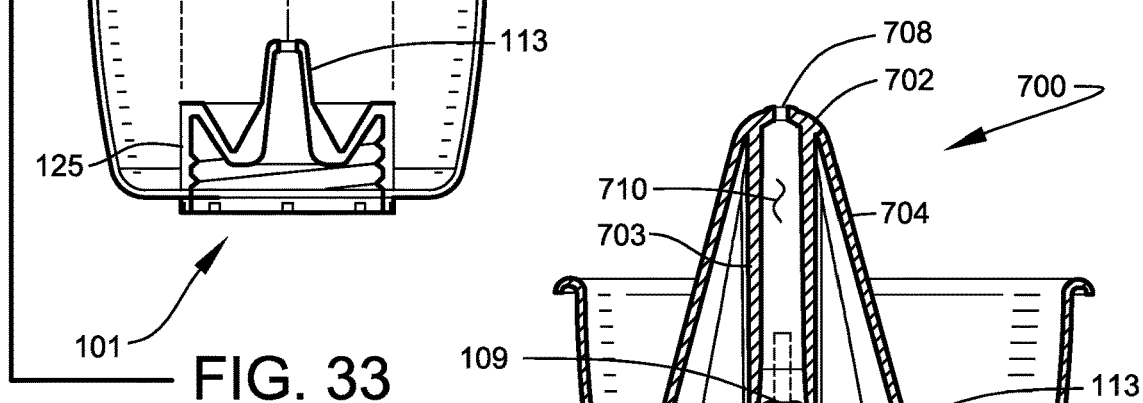
FIG. 33 shows an exploded side view, illustrating a nasal irrigation adapter of the alternate nasal irrigator of FIG. 32.
Figure 34:
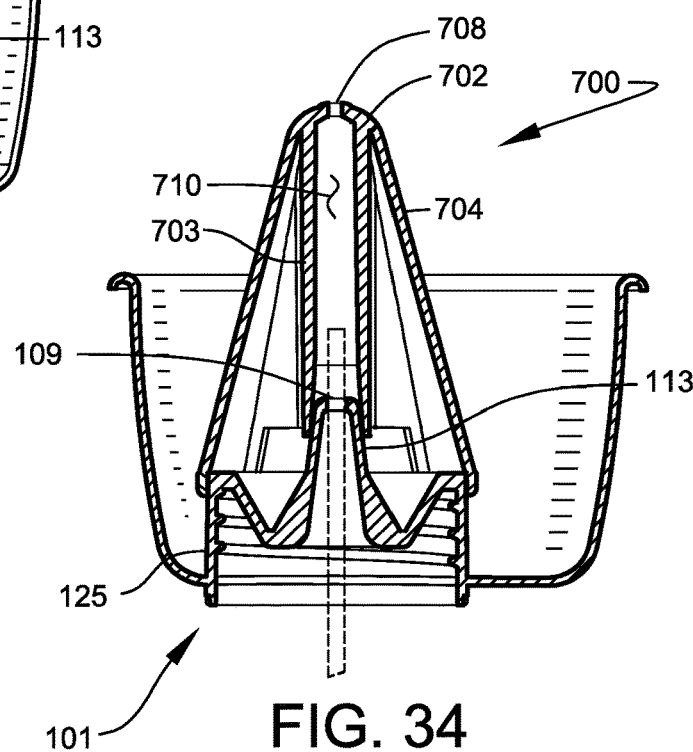
FIG. 34 is a sectional view through the section 34-34 of FIG. 32.

FIG. 33 shows an exploded side view, further illustrating nasal irrigation adapter 701 of alternate nasal irrigator 700. FIG. 34 is a sectional view through the section 34-34 of FIG. 32.

Nasal irrigation adapter 701 is preferably of double-walled construction consisting of a conical outer wall 704 surrounding a cylindrical inner wall 703, as shown. Preferably, outer wall 704 and inner wall 703 are integrally formed from a single constituent material, as shown.

Figure 35:
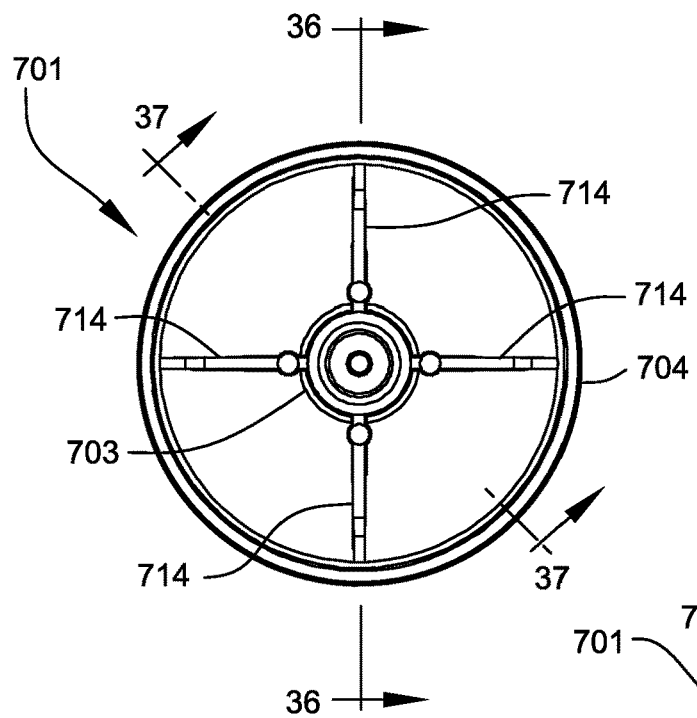
FIG. 35 is a bottom view, further illustrating preferred arrangements of the nasal irrigation adapter, according to the preferred embodiment of FIG. 32.
Figure 36:
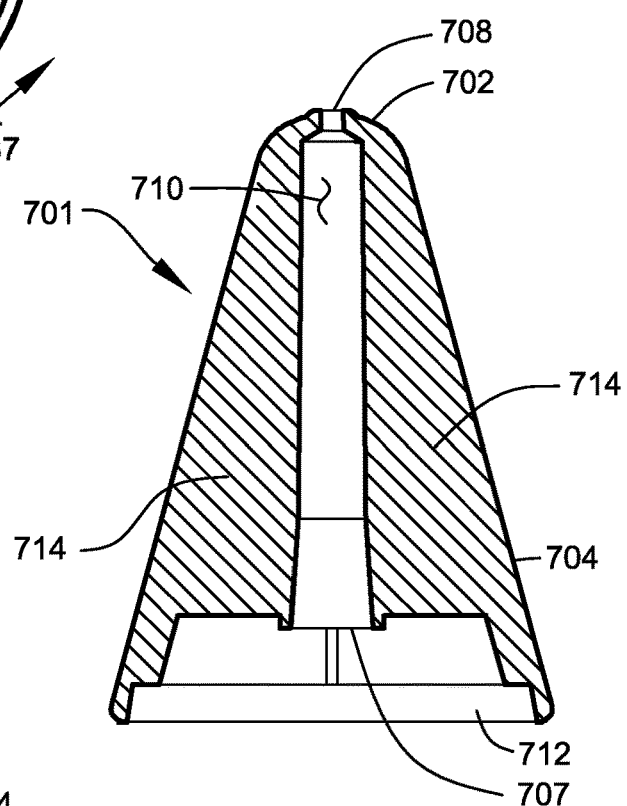
FIG. 36 is a sectional view through the section 36-36 of FIG. 35.
Figure 37:
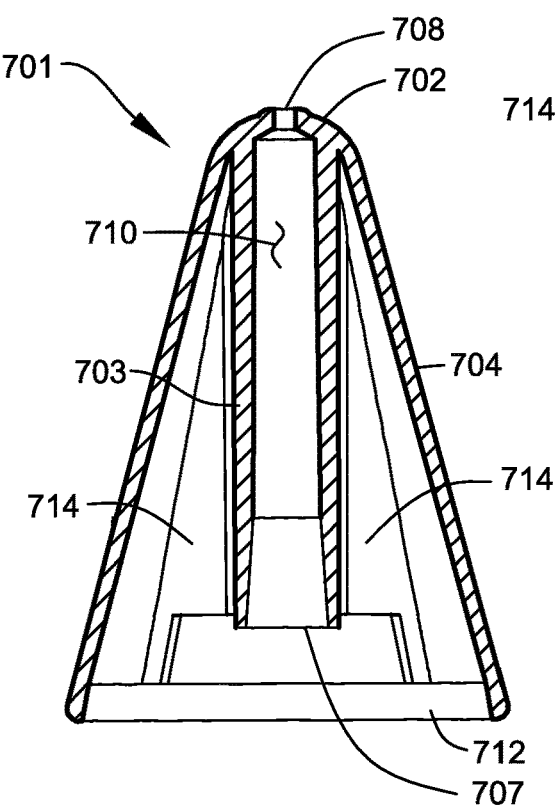
FIG. 37 is a sectional view through the section 37-37 of FIG. 35.

FIG. 35 is a bottom view, further illustrating preferred arrangements of nasal irrigation adapter 700, according to the preferred embodiment of FIG. 32. FIG. 36 is a sectional view through the section 36-36 of FIG. 35. FIG. 37 is a sectional view through the section 37-37 of FIG. 35.

Inner wall 703 preferably comprises an internal bore having a lower open end 707, an upper discharge port 708, and a fluid-transfer channel 710 extending therebetween. Lower open end 707 of the internal bore is preferably configured to engage nozzle portion 113 of ear irrigator 101, as best shown in FIG. 34. Lower open end 712 of outer wall 704 is preferably configured to frictionally engage the outer cylindrical surface of cylinder 125. When nasal irrigation adapter 701 is operably engaged with ear irrigator 101, irrigation liquid exiting nozzle portion 113 is transported through fluid-transfer channel 710 to exit discharge port 708. As previously noted, ear irrigator 101 is structured and arranged to threadably engage the external helical threads of a standard wide-mouth irrigation bottle.

Referring to FIG. 35, the position of inner wall 703 within outer wall 704 and outer shape of outer wall 704 is preferably maintained by a set of four equally-spaced reinforcing panels 714 extending between inner wall 703 and outer wall 704, as shown.

Nasal irrigation adapter 701 is preferably constructed from a non-toxic material suitable for medical use. In one preferred configuration, nasal irrigation adapter 701 preferably comprises a resilient polymer material.

With specific reference to FIGS. 38A-40F, further embodiments of the invention provide a nasal adapter without an effluent collector, which can accommodate at least one, and preferably more than one of a variety of different medical irrigation devices for administration of liquid into a patient's nostril.

Preferably, such nasal adapter without an effluent collector is configured to accommodate at least one, preferably at least more than one of a squirt bottle and syringe. More preferably, such nasal adapter is configured to accommodate at least one, preferably at least more than one of a squirt bottle, a syringe with Luer-Lock connector, and a syringe with Luer-slip-type connector.

Preferably, such nasal adapter is used to administer solution, preferably a sterile liquid saline solution preferably into the patient's nasal passages and sinus cavity for a preferred high flow, low pressure and low volume irrigation.

Preferably, a solution is administered by coupling the connector end of the nasal adapter to the medical irrigation devise, with the medical irrigation devise being at least partially filled with the irrigation liquid, and irrigating the nasal passage by bringing the nasal bulb portion of the nasal adapter into proximity with the nasal passage of the patient, then discharging the irrigation liquid into the nasal passage via a discharging mechanism (e.g. squeezing of the squirt bottle, or pumping of the syringe).

In use, the bulb portion of the nasal adapter assembled with a liquid containing device (e.g. syringe, squirt bottle) is pressed against the patients nostril, and the solution is administered by causing the liquid to be ejected from the device (e.g plunging, squeezing, etc. of the device).

Upon reading the teachings of this specification, those of ordinary skill in the art will understand that, under appropriate circumstances, considering such issues as design preference, user preferences, medical needs, marketing preferences, cost, structural requirements, available materials, technological advances, etc., such nasal adapter without an effluent collector may be configured to accommodate an attachable collector which may or may not include a splash shield (e.g. effluent collector 501 which is attachable between the device and nasal adapter).

Additionally, it is particularly advantageous to provide nasal adapters compatible with both standard wide mouth irrigation pour bottles available in hospitals and standard Luer lock syringes which are widespread in hospitals for use by trained medical personnel, to also be used for nasal irrigation.

Additionally, an adapter for standard wide mouth irrigation pour bottles, which are widespread in hospitals and clinics, can be particularly advantageous as it enables such bottle to be easily used for nasal irrigation. Such bottles typically contain medical grade irrigation fluid and may include features that maintain the sterility of the bottle. Additionally, it may be particularly advantageous to enable an at-home patient to use such bottle provided with sterile solution, as it may reduce potential risk of infection resulting from household water sources which the patient may need to otherwise mix with certain solutions. Thus, a reliable sterile saline source that is readily available and could be used with the disclosed nasal adapter may reduce infection risks for such patients that require irrigations, and is further advantageous for hospital patients with increased susceptibility to invading organisms.

Figure 38A:
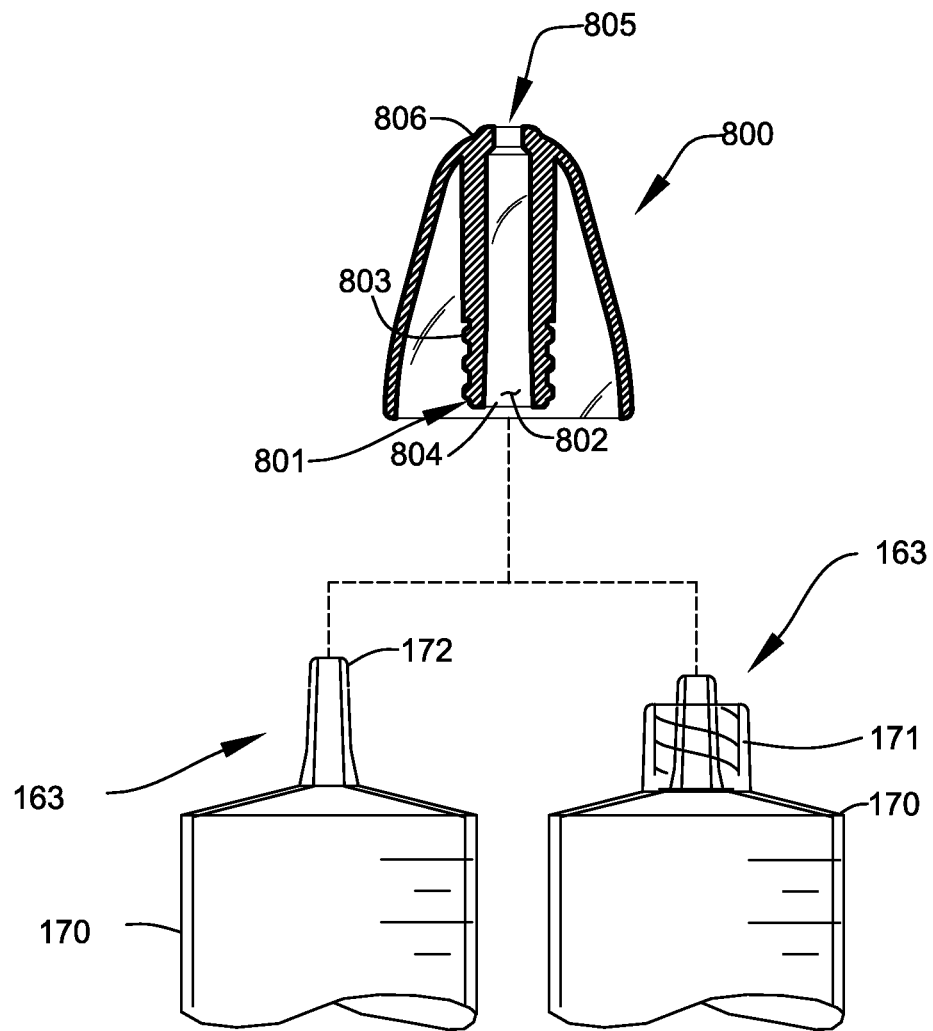
FIG. 38A shows an exploded view, in partial section, illustrating diagrammatically, the coupling of a nasal adapter without effluent collector, configured to connect with one of multiple types of medical syringes, according to a preferred embodiment.

FIG. 38A illustrates a nasal adapter 800, without an effluent collector, comprises a nasal bulb portion 806 forming nasal bulb shaped exterior, and configured to removably connect with medical syringes 170 having either a Luer-lock connector 171 or a Luer-slip-type connector 172, according to a preferred embodiment. Such syringe may preferably be prefilled with a solution, e.g. saline. As shown, nasal adapter 800 comprises interior connector 801 comprising outer Luer threading 803, preferably spiral threading, and interior bore 802 forming Luer taper 804, preferably a female taper generally matching standard 594 of the International Organization for Standardization (ISO).

Nasal bulb portion 806 further comprises discharge port 805 providing a discharge exit for liquid in the syringe when functionally connected to nasal adapter 800. Discharge port 805 preferably comprises a diameter of about ½ mm, preferably a diameter greater than ½ mm. Applicant has found it critical for discharge port 805 to have a larger diameter in order to flood and/or flush nasal passages; smaller diameters cause misting instead of flooding. Upon reading the teachings of this specification, those skilled in the art will now appreciate that, under appropriate circumstances, considering such issues as cost, available materials, etc., other discharge ports, such as, for example, multiple ports, multiple smaller ports discharging similar volumes, etc., may suffice.

Figure 38B:
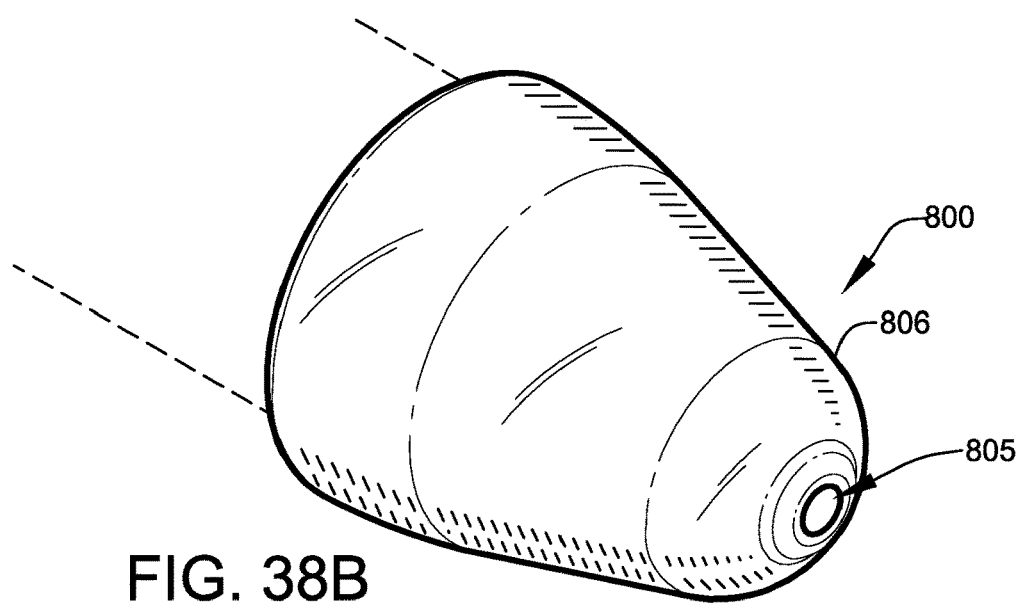
FIG. 38B is a perspective outer view of the nasal adapter of FIG. 38A, depicted as connected to one of said syringes.
Figure 38F:
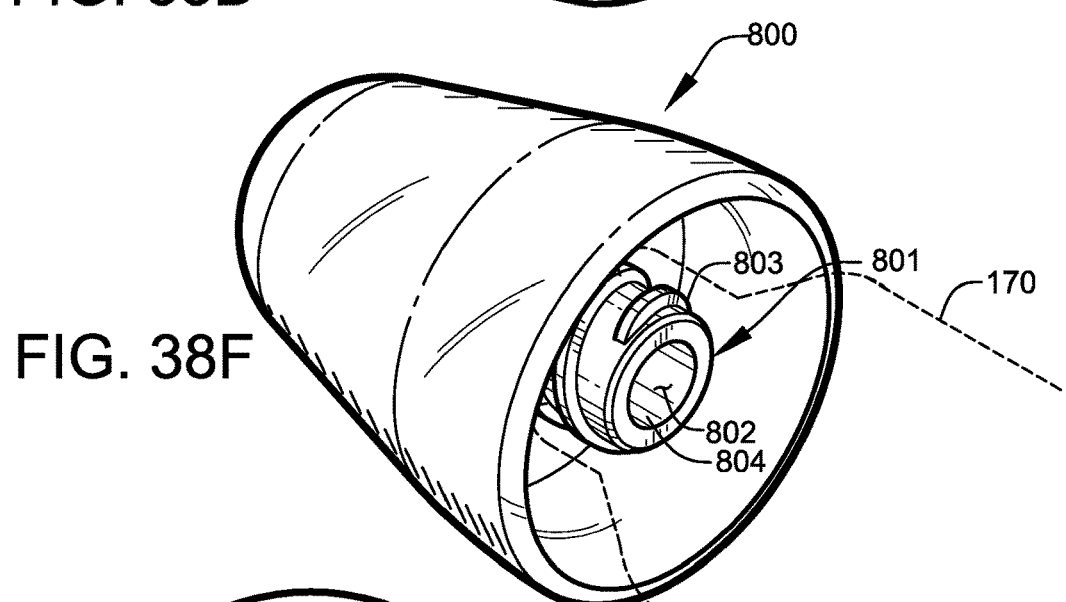
FIG. 38F is a perspective internal view of the nasal adapter of FIG. 38A, depicted in its connected state.
Figure 38D:
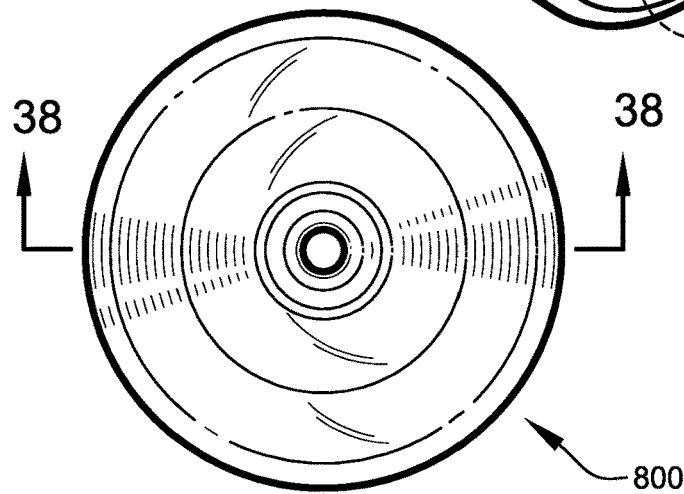
FIG. 38D is a top outer elevation view of the nasal adapter of FIG. 38A.
Figure 38C:
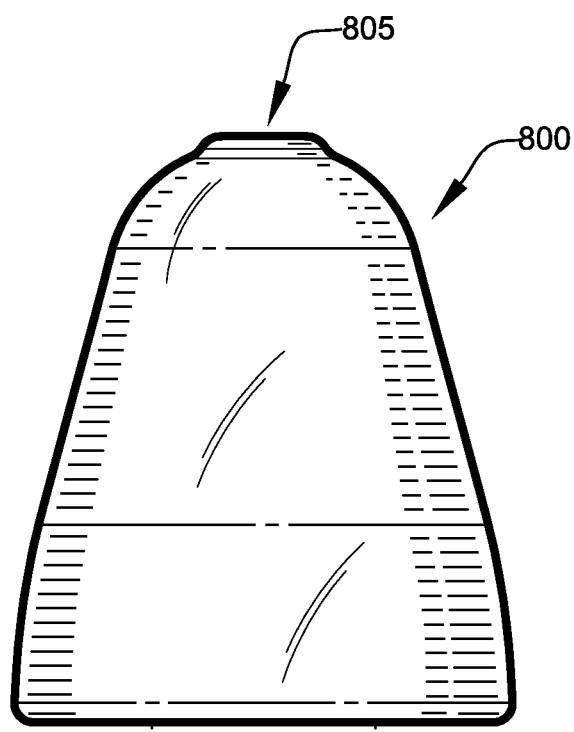
FIG. 38C is a front elevation outer view of the nasal adapter of FIG. 38A, depicted in its connected state.
Figure 38E:
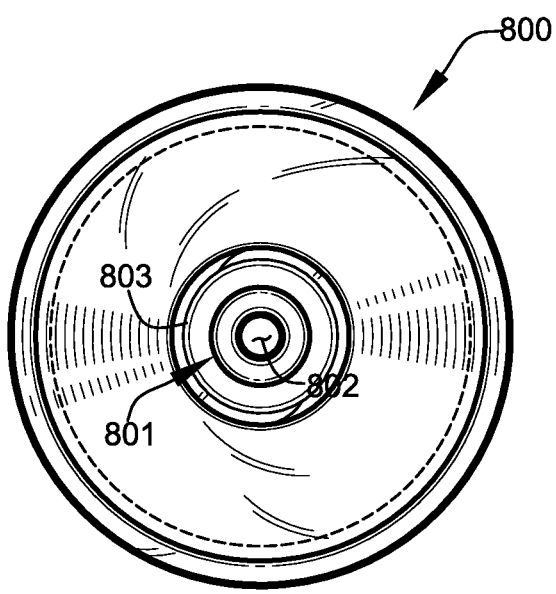
FIG. 38E is a bottom elevation view of the nasal adapter of FIG. 38A.
Figure 38G:
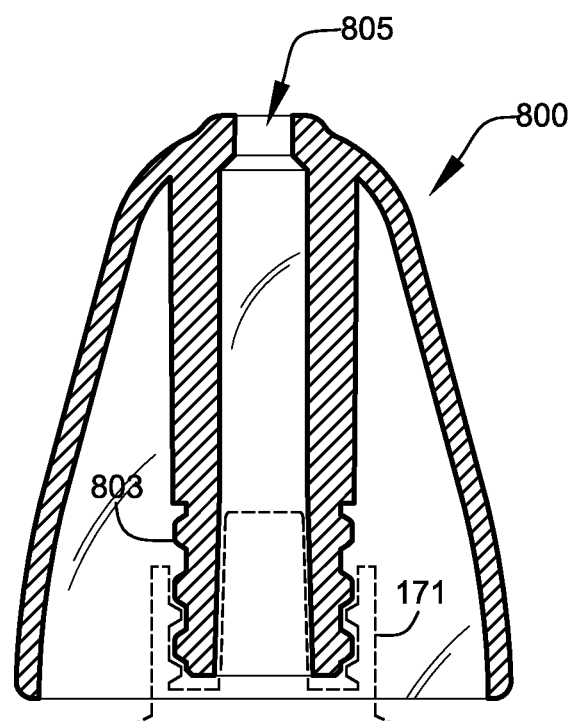
FIG. 38G is a sectional view through section 6-6 of FIG. 38D of the nasal adapter of FIG. 38A, depicted in its connected state.

FIG. 38B is a perspective outer view of nasal adapter 800 depicted as connected to one of syringes 170. FIG. 38C is a front elevation outer view of nasal adapter 800 depicted in its connected configuration. FIG. 38D is a top outer elevation view of the adapter 800. FIG. 38E is a bottom elevation view of adapter 800, illustrating its internal components. FIG. 38F is a perspective internal view of nasal adapter 800 depicted in its connected state. FIG. 38G is a sectional view through section 6-6 of FIG. 38D of adapter 800, depicted as connected to Luer-Lock connector 171 of syringe 170.

Figure 39A:
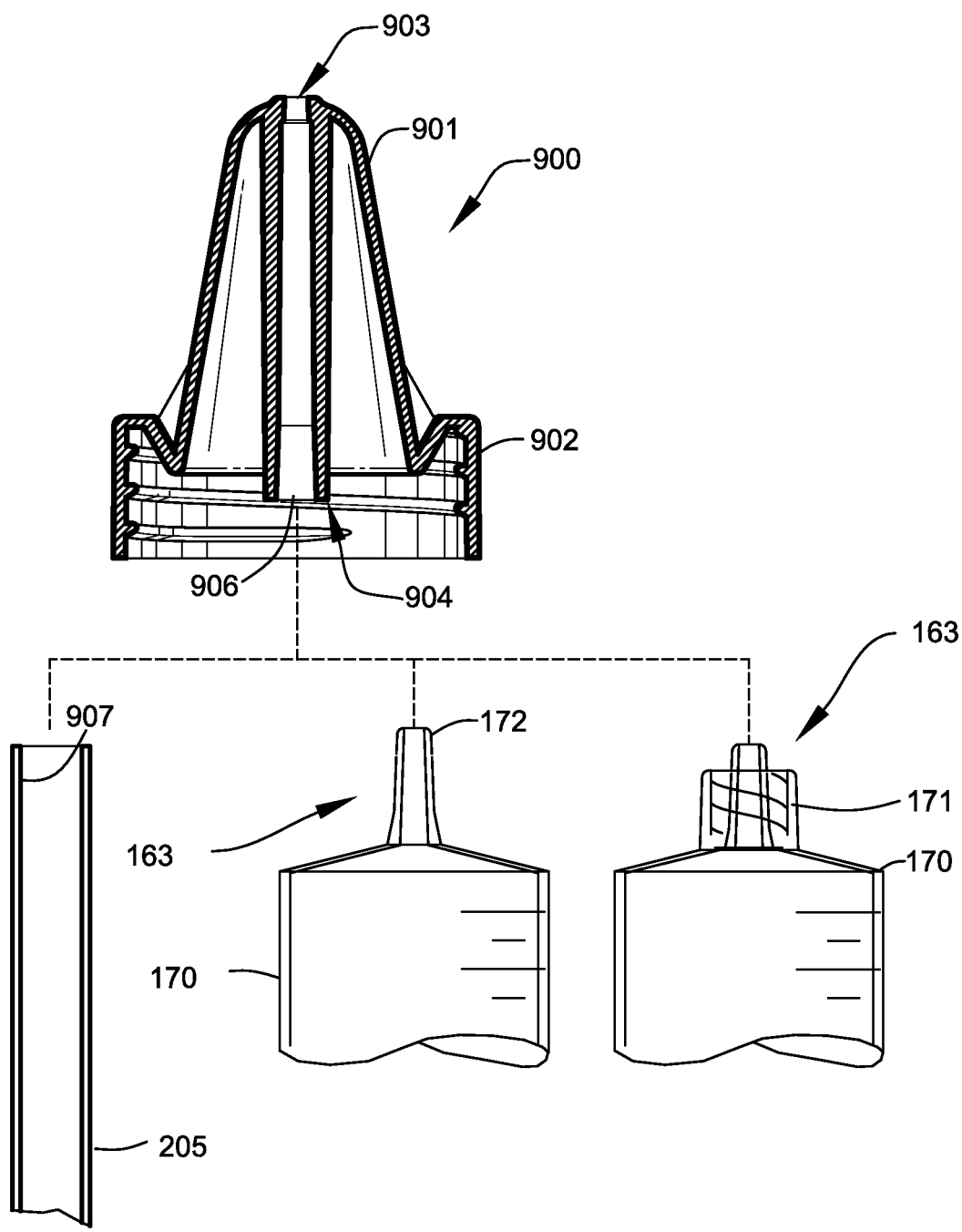
FIG. 39 A shows an exploded view, in partial section, illustrating diagrammatically, the coupling of a nasal adapter without effluent collector, configured to connect with one of multiple types of medical devices comprising a squeeze bottle having a dip tube and syringe having a Luer-slip-type connector, according to a preferred embodiment.

FIG. 39 A illustrates a nasal adapter 900, without an effluent collector, having a bulb portion 901 forming a nasal bulb exterior, and configured to removably connect with dip tube 205 of squeeze bottle 102, or with a medical syringe 170 having a Luer-slip-type connector 172, according to an alternate preferred embodiment. As shown, nasal adapter 900 preferably comprises internally threaded neck 902 structured and arranged to threadably engage the outer threading of squeeze bottle 102. Adapter 900 further comprises interior connector 904 preferably forming Luer taper 906, for capturing the outer taper of connector 172, and alternately sealably engaging the internal walls 907 of dip tube 205 forming a friction fit seal. Nasal bulb portion 901 further comprises discharge port 903 providing a discharge exist for liquid in the syringe or squeeze bottle when functionally connected to nasal adapter 900. Discharge port 903 preferably comprises a diameter of about ½ mm, preferably a diameter greater than ½ mm. Applicant has found it critical for discharge port 903 to have a larger diameter in order to flood and/or flush nasal passages; smaller diameters cause misting instead of flooding. Upon reading the teachings of this specification, those skilled in the art will now appreciate that, under appropriate circumstances, considering such issues as cost, available materials, etc., other discharge ports, such as, for example, multiple ports, multiple smaller ports discharging similar volumes, etc., may suffice. Upon reading the teachings of this specification, those of ordinary skill in the art will now understand that, under appropriate circumstances, considering such issues as leakage prevention, dip tube and syringe design, a nasal adapter configured to connect with a dip tube, as well as syringes with either a Luer-slip or Luer-lock, may suffice.

Figure 39B:
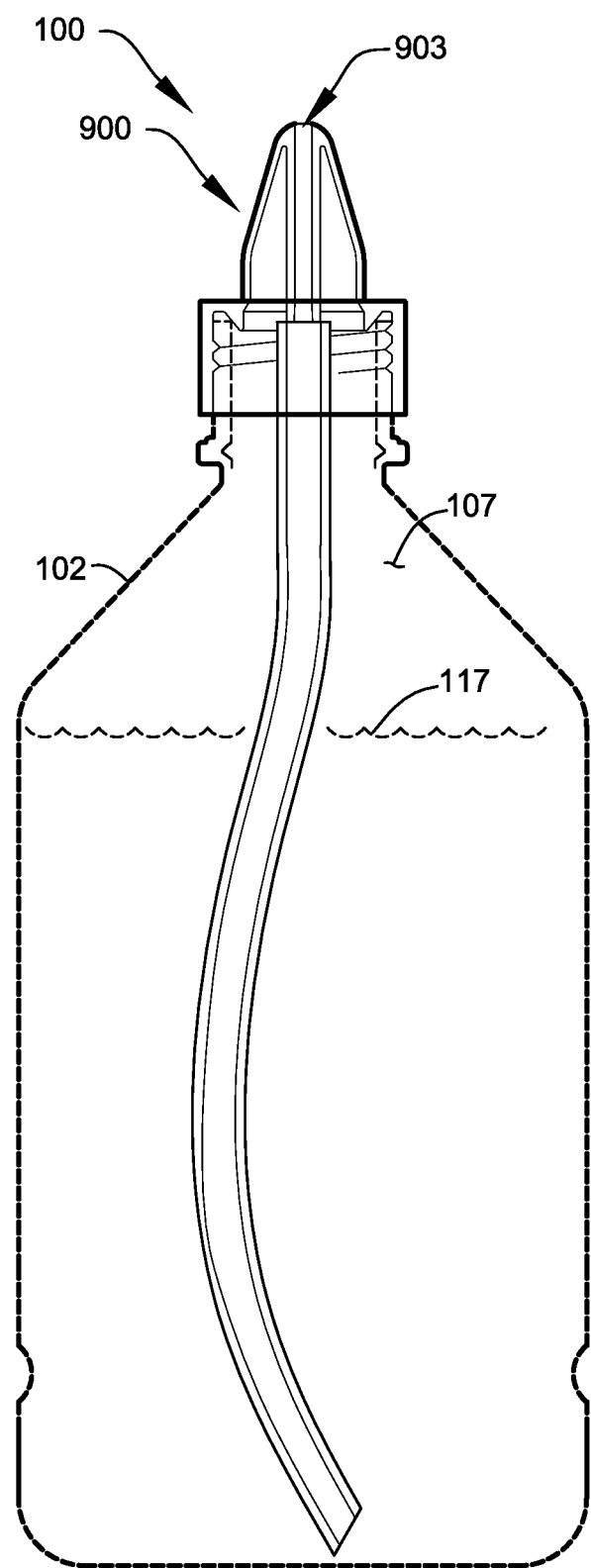

FIG. 39B shows adapter 900 connected to squeeze bottle 102 with the interior connector 904 of adapter 900 fitted with dip tube 205.

FIGS. 40A-40F illustrate an adapter 910, similar to adapter 900, having an preferred fanciful design comprising a plurality of spaced apart ribs 912 between the bulb portion 901 and neck 902, as shown.

Figure 40A:
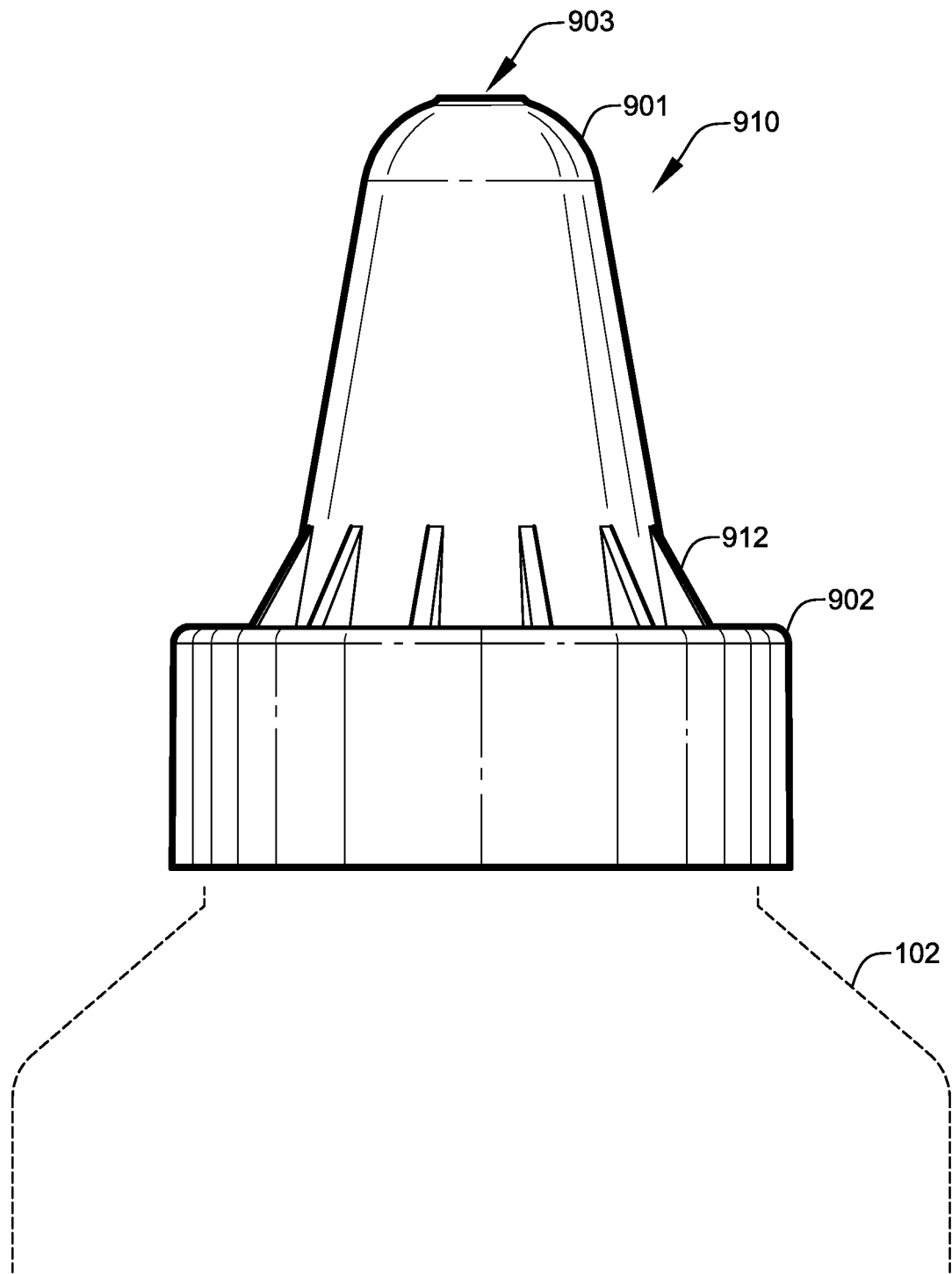
FIG. 40A is a perspective view of an adapter, similar to the adapter of FIG. 39A, having a fanciful design comprising ribs, according to a preferred embodiment.
Figure 40B:
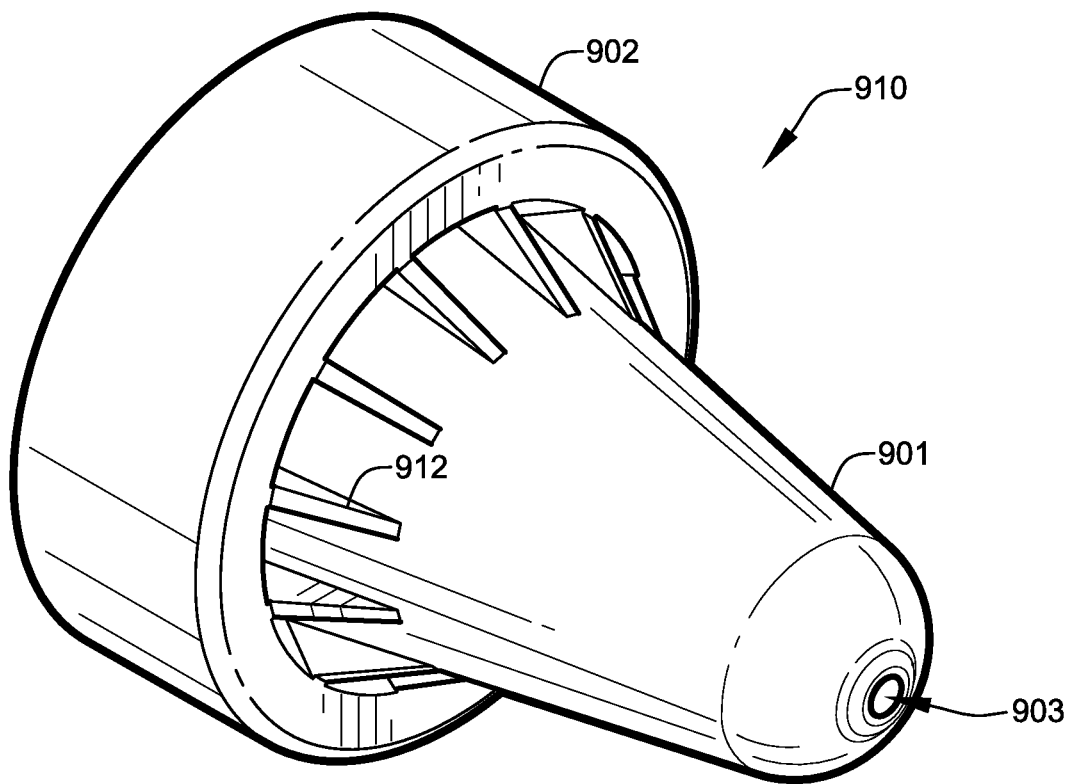
FIG. 40B is a top or exterior perspective view of the adapter of FIG. 40A.
Figure 40C:
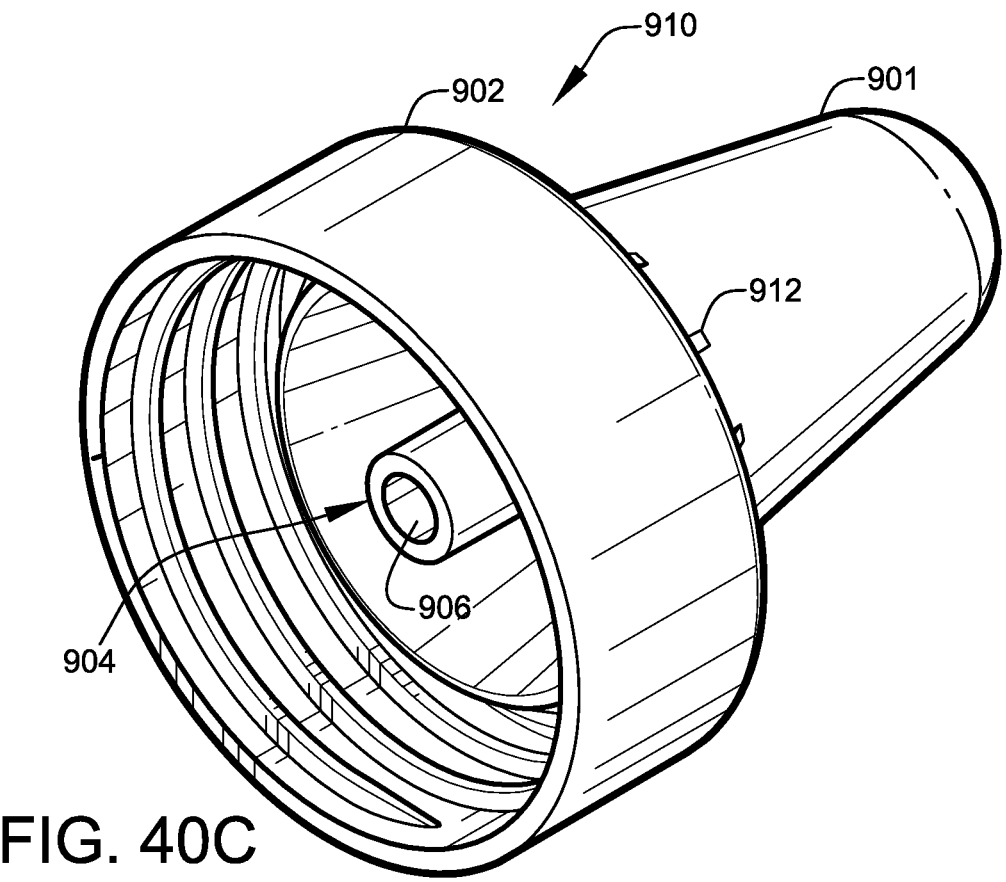
FIG. 40C is a perspective bottom or interior view of the adapter of FIG. 40A.
Figure 40D:
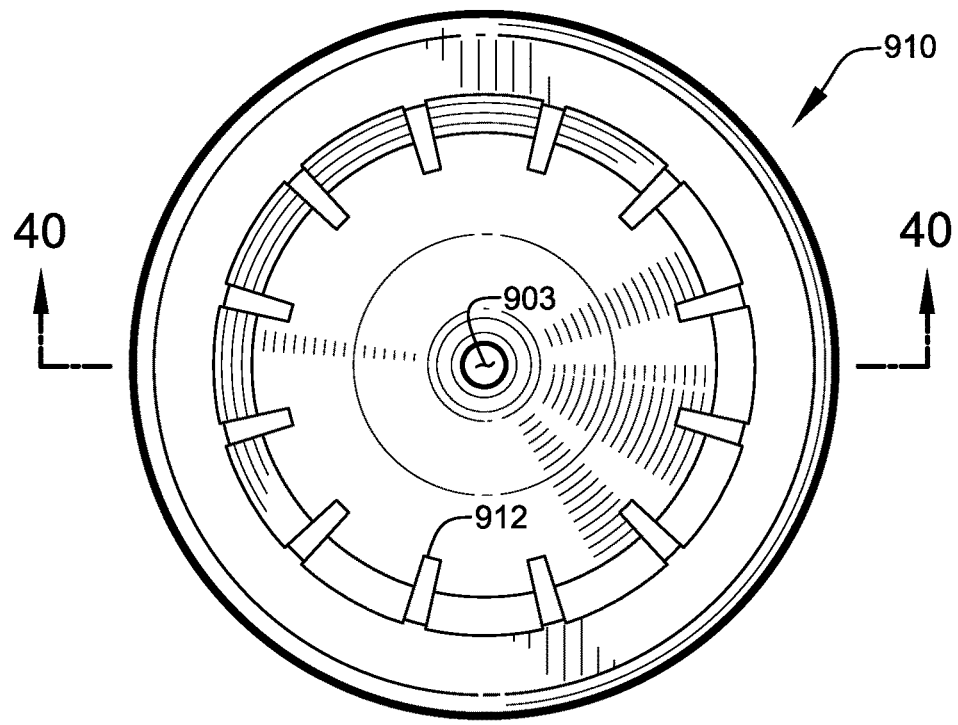
FIG. 40D is a top or exterior plan view of the adapter of FIG. 40A.
Figure 40E:
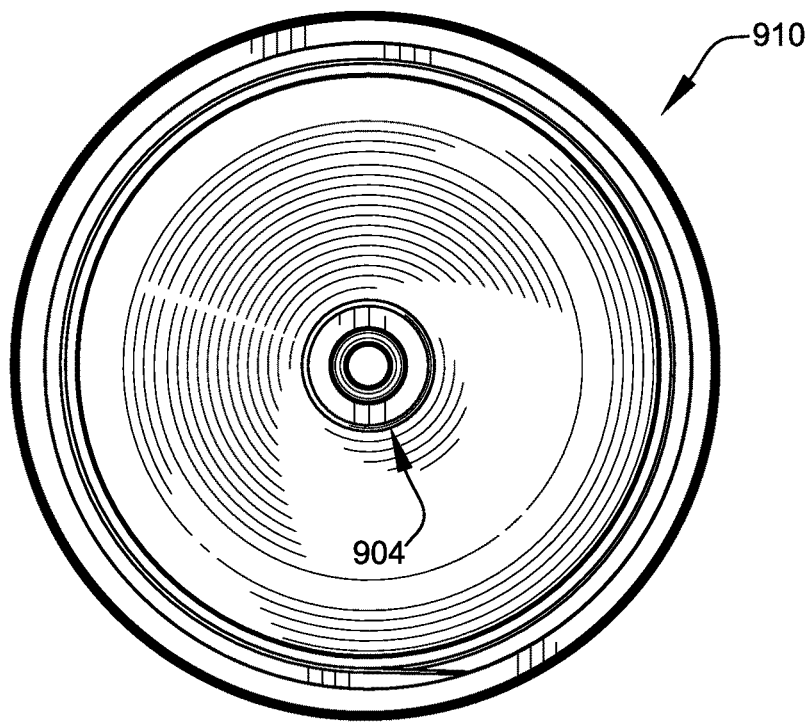
FIG. 40E is a bottom or interior plan view of the adapter of FIG. 40A.
Figure 40F:
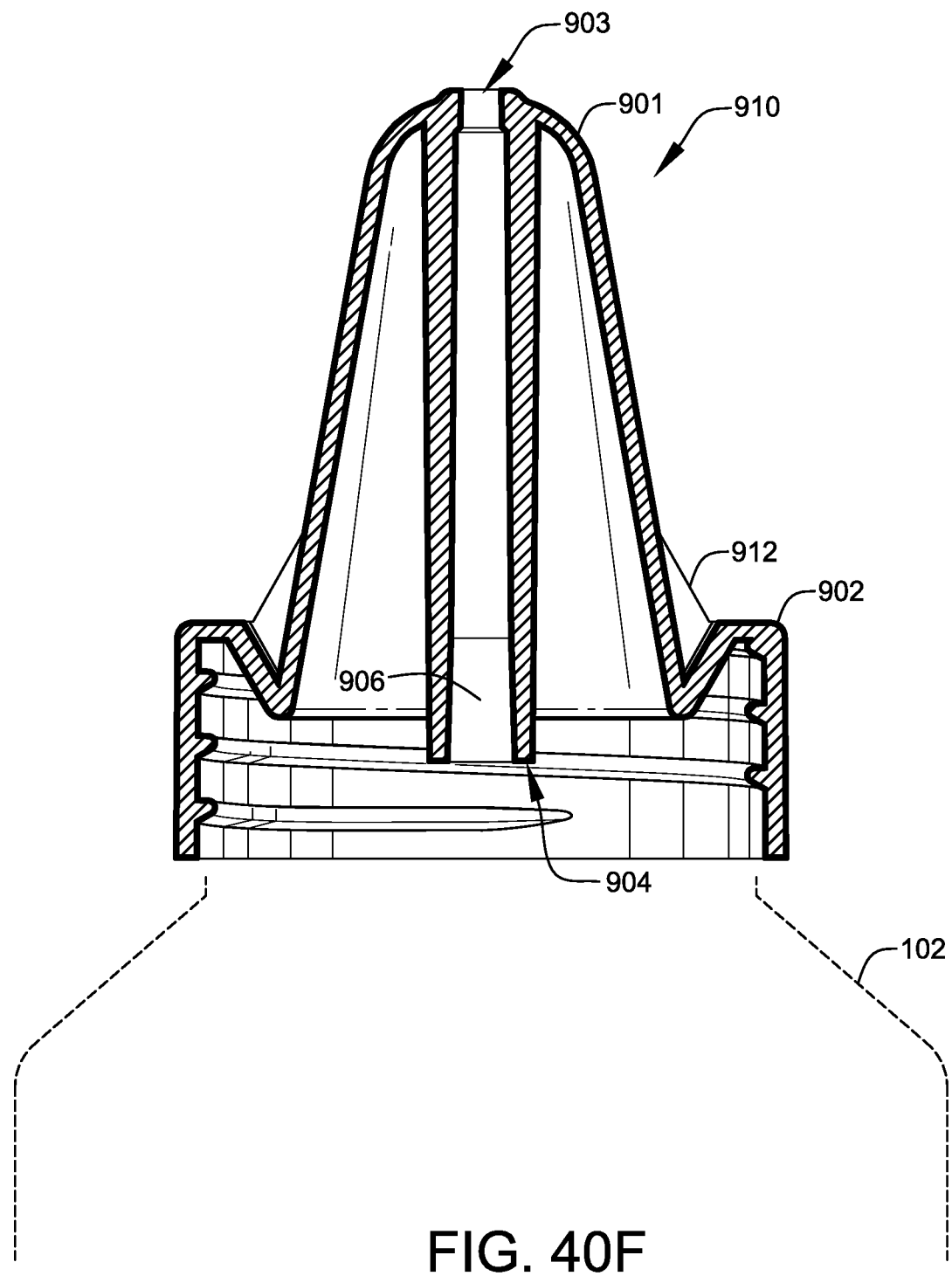
FIG. 40F is a sectional view of the adapter of FIG. 40A through section 6-6 of FIG. 40D, depicted as connected to the squeeze bottle.

FIG. 40A is a perspective view of adapter 910, depicted as connected to squeeze bottle 102. FIG. 40B is a top or exterior presective view of adapter 910. FIG. 40C is a perspective bottom or interior view thereof. FIG. 40D is a top or exterior plan view of adapter 910. FIG. 40E is a bottom or interior plan view thereof. FIG. 40F is a sectional view through section 6-6 of FIG. 40D of adapter 910, depicted as connected to squeeze bottle 102.

As will be understood by one skilled in the art, the above described adapter may be specifically designed to provide certain advantageous depending on the desired use and specific needs. For example, the nasal adapter of the present invention is preferably structured and arranged to accommodate large syringes with volumes preferably greater than 15 ml, preferably with prefilled sterile saline and a distal nasal adapter that could be used in some cases for large volume irrigation for example the nasal passages of an adult.

In another example, the described nasal adapter may be structured and arranged to specifically accommodate small volume prefilled preferably saline flush syringes, e.g. preferably around 5 ml, or 10 ml, for use with smaller pediatric or neonatal patients. This is particularly advantageous as larger volume bottle irrigation can be inappropriate for small children due to the inability to control the volume, including the limiting the volume. Additionally, such adapter can be designed to have a wide body for preventing risk associated with the adapter accidentally falling into a child's mouth.

Additionally, according to certain embodiments, the nasal adapter may be specifically structured to be easily attached and difficult to accidently remove. In some cases it would be desirable to have a syringe with a commonly used adapter, such as a Luer and Luer lock adapters, since the syringes would be readily available in medical facilities by trained personnel. Luer lock adapters are particularly useful due to their ability to retain an attached adapter from pulling forces. In other cases it might be useful to have non-Luer tipped syringes to avoid any connector misconnects or incompatibility to avoid medical errors, such as when oral syringes have been used for oral medication administration.

Although applicant has described applicant's preferred embodiments of this invention using metric standardized units, such measurements have been provided only for the convenience of the reader and should not be read as controlling or limiting. Instead, the reader should interpret any measurements provided in English standardized units as controlling. Any measurements provided in metric standardized units were merely derived through strict mechanical coding, with all converted values rounded to two decimal places.

Although applicant has described applicant's preferred embodiments of this invention, it will be understood that the broadest scope of this invention includes modifications such as diverse shapes, sizes, and materials. Such scope is limited only by the below claims as read in connection with the above specification. Further, many other advantages of applicant's invention will be apparent to those skilled in the art from the above descriptions and the below claims.

What is claimed is:

1. A non-sterile system, relating to procedures involving flushing of the nasal passages using at least one irrigation liquid, comprising:
   a pre-filled plunger syringe comprising a volume of at least 5 mL of a salt solution;
   at least one liquid injector structured and arranged to assist rapid flushing of at least 5 mL of liquid through at least one nasal passage;
   a nasal anatomical adapter defined by a distal end and a proximal end, the nasal anatomical adapter being structured and arranged to form a liquid seal between the nasal anatomical adapter distal end and the anatomical geometry of at least one nostril; and
   wherein the at least one liquid injector comprises at least one coupler to couple and form a liquid seal between said at least one injector and the plunger syringe.

2. The system according to claim 1 wherein said at least one coupler comprises a female Luer connector.

3. The system according to claim 1, wherein said at least one coupler comprises a female Luer lock connector.

4. The system according to claim 1 wherein said at least one coupler is incompatible with a male Luer lock syringe.

5. The system according to claim 1 wherein said at least one anatomical adapter and said at least one coupler are molded as a single monolithic piece.

6. The system according to claim 1 wherein said at least one injector comprises an outlet port with an outlet cross-sectional area greater than the cross-sectional area of a circle with a diameter of ½ mm.

7. The system according to claim 1 wherein the at least one injector comprises an outlet port comprising a cylindrical aperture.

8. The system according to claim 1 wherein said plunger syringe comprises a liquid volume of less than 15 mL.

9. The system according to claim 1 wherein said plunger syringe comprises a liquid volume of at least 15 mL.

10. The system according to claim 1 wherein the salt solution comprises sterile saline.

11. The system according to claim 1 further comprising at least one effluent collector structured and arranged to collect effluent draining from the at least one nasal passage.

12. The system according to claim 1 wherein:
   a) said at least one anatomical adapter comprises an outer wall and an inner hollow;
   b) said at least one coupler extends from said at least one anatomical adapter and terminates within said inner hollow;
   c) said at least one coupler comprises a Luer connector; and
   d) said at least one anatomical adapter, said at least one injector and said at least one coupler comprise a single monolithic molded piece.

13. The system according to claim 1 wherein:
   a) said at least one anatomical adapter comprises an outer wall and an inner hollow;
   b) said at least one coupler extends from said at least one anatomical adapter and terminates within said hollow;
   c) said at least one coupler comprises a Luer lock connector; and
   d) said at least one anatomical adapter, said at least one injector and said at least one coupler comprise a single monolithic molded piece.

14. The system of claim 1, wherein the plunger syringe comprises a male luer-lock connector.

15. The system according to claim 1, wherein:
   said at least one anatomical adapter comprises an outer wall and an inner wall that defines an inner hollow;
   said at least one liquid injector extends from said at least one anatomical adapter inner wall and terminates within said inner hollow; and
   said at least one coupler comprises a Luer connector.

16. The system of claim 1, wherein the liquid injector is configured to generate a stream of irrigation liquid.

17. The system of claim 1, wherein the nasal anatomical adapter distal end defines a truncated shape.

18. The system of claim 1, wherein the nasal anatomical adapter distal end defines a blunt end bulb configured to sealingly engage a nostril to prevent further entry past the nostril.

19. The system of claim 1, wherein the plunger syringe comprises a catheter-tip connector to operably connect with the at least one coupler.

20. The system of claim 1, wherein said at least one injector comprises multiple discharge ports.

21. The system of claim 1, wherein the salt solution consists of salt water solution.

22. The system of claim 1, wherein the salt solution consists of saline solution.

23. The system of claim 1, wherein the salt solution consists of normal saline solution.

24. A method for flushing at least one nasal passage extending between a first nostril and a second nostril, the method comprising:
flushing a continuous volume of a salt solution from a pre-filled plunger syringe into a first nostril so that the continuous volume of salt solution exits out of a second nostril, wherein the continuous volume of salt solution is from 5 mL to 15 mL.

25. The method of claim 24, wherein the plunger syringe supports a nasal adapter to form a seal with the first nostril.

26. The method of claim 24, wherein the flushing step is conducted on an infant or neonatal patient.

27. The method of claim 24, wherein the salt solution consists of salt water solution.

28. The method of claim 24, wherein the salt solution consists of saline solution.

29. The method of claim 24, wherein the salt solution consists of normal saline solution.

30. The method of claim 24, wherein the volume of salt solution is sterile.

31. A system, relating to procedures involving flushing of the nasal passages, through a first nostril and out a second nostril, using at least one irrigation liquid, the system consisting of:
a plunger syringe comprising a volume of from 5 mL to 15 mL;
a liquid injector structured and arranged to assist rapid flushing of at least 5 mL of liquid through at least one nasal passage;
a nasal anatomical adapter structured and arranged to form a liquid seal between said at least one liquid injector and only the anatomical geometry of at least one nostril, the nasal anatomical adapter defining an inner hollow extending between a distal end and a proximal end; and
at least one coupler structured and arranged to couple and form a liquid seal between said at least one injector and the plunger syringe, the at least one coupler being radially separated from the nasal anatomical adapter by the inner hollow.

32. The system of claim 31, wherein the nasal anatomical adapter proximal end extends beyond the at least one coupler so that the at least one coupler is entirely surrounded by the nasal anatomical adapter.

33. The system of claim 31, wherein the at least one irrigation liquid consists of saline.

34. The system of claim 31, wherein the plunger syringe comprises a male luer connector, and the at least one coupler is a female luer connector.

* * * * *